(12) United States Patent
Thorne

(10) Patent No.: US 8,742,072 B2
(45) Date of Patent: Jun. 3, 2014

(54) BONE GROWTH PARTICLES AND OSTEOINDUCTIVE COMPOSITION THEREOF

(75) Inventor: Kevin J. Thorne, Austin, TX (US)

(73) Assignee: Zimmer Orthobiologics, Inc., Austin, TX (US)

( * ) Notice: Subject to any disclaimer, the term of this patent is extended or adjusted under 35 U.S.C. 154(b) by 0 days.

(21) Appl. No.: 12/748,999

(22) Filed: Mar. 29, 2010

(65) Prior Publication Data

US 2010/0196489 A1 Aug. 5, 2010

Related U.S. Application Data

(63) Continuation of application No. 11/614,422, filed on Dec. 21, 2006, now Pat. No. 7,718,616.

(51) Int. Cl.
*A61K 38/17* (2006.01)
*A61K 33/42* (2006.01)
*A61K 9/14* (2006.01)
*A01N 59/26* (2006.01)

(52) U.S. Cl.
USPC .......... 530/356; 514/21.2; 424/602; 424/603; 424/489

(58) Field of Classification Search
USPC ........ 530/356; 514/2, 12, 21.2; 424/602, 603, 424/489
See application file for complete search history.

(56) References Cited

U.S. PATENT DOCUMENTS

| | | |
|---|---|---|
| 2,471,598 A | 5/1949 | Wilt et al. |
| 3,368,911 A | 2/1968 | Kuntz et al. |
| 3,393,080 A | 7/1968 | Erdi et al. |
| 3,443,261 A | 5/1969 | Battista et al. |
| 3,471,598 A | 10/1969 | Battista et al. |
| 3,767,437 A | 10/1973 | Cruz, Jr. |
| 3,919,723 A | 11/1975 | Heimke et al. |
| 3,949,073 A | 4/1976 | Daniels et al. |
| 3,968,567 A | 7/1976 | Nevins |
| 4,066,083 A | 1/1978 | Ries |
| 4,131,597 A | 12/1978 | Bluethgen et al. |
| 4,146,936 A | 4/1979 | Aoyagi et al. |
| 4,191,747 A | 3/1980 | Scheicher |
| 4,192,021 A | 3/1980 | Deibig et al. |
| 4,202,055 A | 5/1980 | Reiner et al. |
| 4,233,360 A | 11/1980 | Luck et al. |
| 4,237,559 A | 12/1980 | Borom |
| 4,273,705 A | 6/1981 | Kato |
| 4,294,753 A | 10/1981 | Urist |
| 4,356,572 A | 11/1982 | Guillemin et al. |
| 4,389,487 A | 6/1983 | Ries |
| 4,394,370 A | 7/1983 | Jefferies |
| 4,412,947 A | 11/1983 | Cioca |
| 4,429,691 A | 2/1984 | Niwa et al. |
| 4,430,760 A | 2/1984 | Smestad |
| 4,440,680 A | 4/1984 | Cioca |
| 4,440,750 A | 4/1984 | Glowacki et al. |
| 4,451,397 A | 5/1984 | Huc et al. |
| 4,455,256 A | 6/1984 | Urist |
| 4,472,840 A | 9/1984 | Jefferies |
| 4,485,097 A | 11/1984 | Bell |
| 4,497,075 A | 2/1985 | Niwa et al. |
| 4,516,276 A | 5/1985 | Mittelmeier et al. |
| 4,557,764 A | 12/1985 | Chu |
| 4,563,350 A | 1/1986 | Nathan et al. |
| 4,563,489 A | 1/1986 | Urist |
| 4,596,574 A | 6/1986 | Urist |
| 4,600,533 A | 7/1986 | Chu |
| 4,606,910 A | 8/1986 | Sawyer |
| 4,609,551 A | 9/1986 | Caplan et al. |
| 4,619,655 A | 10/1986 | Hanker et al. |
| 4,619,989 A | 10/1986 | Urist |
| 4,620,327 A | 11/1986 | Caplan et al. |
| 4,623,553 A | 11/1986 | Ries et al. |
| 4,629,464 A | 12/1986 | Takata et al. |
| 4,637,931 A | 1/1987 | Schmitz |
| 4,642,120 A | 2/1987 | Nevo et al. |
| 4,656,130 A | 4/1987 | Shoshan |
| 4,668,295 A | 5/1987 | Bajpai |
| 4,689,399 A | 8/1987 | Chu |
| 4,693,986 A | 9/1987 | Vit et al. |
| 4,698,326 A | 10/1987 | Sauk et al. |
| 4,703,108 A | 10/1987 | Silver et al. |

(Continued)

FOREIGN PATENT DOCUMENTS

| | | |
|---|---|---|
| AU | 2007334213 B2 | 8/2012 |
| CA | 2133253 A1 | 3/1996 |

(Continued)

OTHER PUBLICATIONS

Noah, E.M., et al, "Impact of Sterilization on the Porpus Design and Cell Behavior in Collagen Sponges prepared for Tissue Engineering," Biomaterials, 2002, vol. 23, Elsevier.
"U.S. Appl. No. 12/180,035, Non Final Office Action mailed Nov. 28, 2012", 9 pgs.
"U.S. Appl. No. 12/849,414 , Response filed Nov. 1, 2012 to Final Office Action mailed Aug. 1, 2012", 8 pgs.
"U.S. Appl. No. 12/849,414, Final Office Action mailed Aug. 1, 2012", 20 pgs.
"U.S. Appl. No. 13/297,005, Non Final Office Action mailed Oct. 10, 2012", 13 pgs.
"U.S. Appl. No. 13/297,005, Response filed Jan. 10, 2013 to Non Final Office Action mailed Oct. 10, 2012", 10 lpgs.
"Canadian Application Serial No. 2,673,337, Office Action mailed Sep. 9, 2012", 3 pgs.
"Japanese Application Serial No. 1998535914, Response filed Jul. 24, 2012 to Office Action mailed Jan. 24, 2012", (w/ English Translation of Claims), 16 pgs.
"Japanese Application Serial No. 2009-543018, Office Action mailed Dec. 4, 2012", (w/ English Translation), 5 pgs.

(Continued)

*Primary Examiner* — Chih-Min Kam
(74) *Attorney, Agent, or Firm* — Schwegman Lundberg & Woessner, P.A.

(57) ABSTRACT

A biocompatible synthetic bone growth composition comprising a fibrillar collagen component and a calcium phosphate component. The composition is formed into particles, and then formed into a unitary article that may be provided at the site of a skeletal defect. An osteoinductive component may be further added, either before or after forming the unitary article. The composition may be formulated as a paste or putty and facilitates bone growth and/or repair.

24 Claims, 1 Drawing Sheet

(56) References Cited

U.S. PATENT DOCUMENTS

| | | |
|---|---|---|
| 4,725,671 A | 2/1988 | Chu et al. |
| 4,743,229 A | 5/1988 | Chu |
| 4,761,471 A | 8/1988 | Urist |
| 4,774,227 A | 9/1988 | Piez et al. |
| 4,774,228 A | 9/1988 | Seyedin et al. |
| 4,774,322 A | 9/1988 | Seyedin et al. |
| 4,776,890 A | 10/1988 | Chu |
| 4,780,450 A | 10/1988 | Sauk et al. |
| 4,789,663 A | 12/1988 | Wallace et al. |
| 4,789,732 A | 12/1988 | Urist |
| 4,795,467 A | 1/1989 | Piez et al. |
| 4,795,804 A | 1/1989 | Urist |
| 4,804,744 A | 2/1989 | Sen |
| 4,810,691 A | 3/1989 | Seyedin et al. |
| 4,839,215 A | 6/1989 | Starling et al. |
| 4,843,063 A | 6/1989 | Seyedin et al. |
| 4,843,112 A | 6/1989 | Gerhart et al. |
| 4,846,838 A | 7/1989 | Takai et al. |
| 4,863,732 A | 9/1989 | Nathan et al. |
| 4,863,856 A | 9/1989 | Dean, Jr. et al. |
| 4,865,602 A | 9/1989 | Smestad et al. |
| 4,888,366 A | 12/1989 | Chu et al. |
| 4,891,359 A | 1/1990 | Saferstein et al. |
| 4,919,670 A | 4/1990 | Dale et al. |
| 4,948,540 A | 8/1990 | Nigam |
| 4,950,483 A | 8/1990 | Ksander et al. |
| 4,970,298 A | 11/1990 | Silver et al. |
| 4,975,526 A | 12/1990 | Kuberasampath et al. |
| 4,975,527 A | 12/1990 | Koezuka et al. |
| 4,992,226 A | 2/1991 | Piez et al. |
| 4,997,446 A | 3/1991 | Thoma |
| 5,001,169 A | 3/1991 | Nathan et al. |
| 5,011,691 A | 4/1991 | Oppermann et al. |
| 5,024,841 A | 6/1991 | Chu et al. |
| 5,028,695 A | 7/1991 | Eckmayer et al. |
| 5,034,059 A | 7/1991 | Constantz |
| 5,035,715 A | 7/1991 | Smestad et al. |
| 5,047,031 A | 9/1991 | Constantz |
| 5,053,212 A | 10/1991 | Constantz et al. |
| 5,061,286 A | 10/1991 | Lyle |
| 5,069,905 A | 12/1991 | Lidor et al. |
| 5,071,434 A | 12/1991 | Tsuzuki et al. |
| 5,071,436 A | 12/1991 | Huc et al. |
| 5,073,373 A | 12/1991 | O'Leary et al. |
| 5,084,051 A | 1/1992 | Tormala et al. |
| 5,085,861 A | 2/1992 | Gerhart et al. |
| 5,090,815 A | 2/1992 | Bohle |
| 5,106,748 A | 4/1992 | Wozney et al. |
| 5,108,436 A | 4/1992 | Chu et al. |
| 5,108,753 A | 4/1992 | Kuberasampath et al. |
| 5,110,604 A | 5/1992 | Chu et al. |
| 5,118,667 A | 6/1992 | Adams et al. |
| 5,123,923 A | 6/1992 | Pommier et al. |
| 5,123,925 A | 6/1992 | Smestad et al. |
| 5,133,755 A | 7/1992 | Brekke et al. |
| 5,137,534 A | 8/1992 | Sumita |
| 5,152,836 A | 10/1992 | Hirano et al. |
| 5,154,931 A | 10/1992 | Kruger et al. |
| 5,158,934 A | 10/1992 | Ammann et al. |
| 5,162,114 A | 11/1992 | Kuberasampath et al. |
| 5,169,837 A | 12/1992 | Lagarde et al. |
| 5,171,574 A | 12/1992 | Kuberasampath et al. |
| 5,171,579 A | 12/1992 | Ron et al. |
| 5,204,382 A | 4/1993 | Wallace et al. |
| 5,206,023 A | 4/1993 | Hunziker |
| 5,207,710 A | 5/1993 | Chu et al. |
| 5,208,219 A | 5/1993 | Ogawa et al. |
| 5,231,169 A | 7/1993 | Constantz et al. |
| 5,236,456 A | 8/1993 | O'Leary et al. |
| 5,236,704 A | 8/1993 | Fujioka et al. |
| 5,246,457 A | 9/1993 | Piez et al. |
| 5,258,029 A | 11/1993 | Chu et al. |
| 5,262,166 A | 11/1993 | Liu et al. |
| 5,263,985 A | 11/1993 | Bao et al. |
| 5,270,300 A | 12/1993 | Hunziker |
| 5,273,964 A | 12/1993 | Lemons |
| 5,274,078 A | 12/1993 | Wada et al. |
| 5,279,831 A | 1/1994 | Constantz et al. |
| 5,290,494 A | 3/1994 | Coombes et al. |
| 5,290,558 A | 3/1994 | O'Leary et al. |
| 5,290,763 A | 3/1994 | Poser et al. |
| 5,304,577 A | 4/1994 | Nagata et al. |
| 5,306,303 A | 4/1994 | Lynch |
| 5,314,476 A | 5/1994 | Prewett et al. |
| 5,320,844 A | 6/1994 | Liu |
| 5,332,802 A | 7/1994 | Kelman et al. |
| 5,336,264 A | 8/1994 | Constanz et al. |
| 5,338,772 A | 8/1994 | Bauer et al. |
| 5,344,654 A | 9/1994 | Rueger et al. |
| 5,352,715 A | 10/1994 | Wallace et al. |
| 5,354,557 A | 10/1994 | Oppermann et al. |
| 5,356,629 A | 10/1994 | Sander et al. |
| 5,364,839 A | 11/1994 | Gerhart et al. |
| 5,366,498 A | 11/1994 | Brannan et al. |
| 5,366,508 A | 11/1994 | Brekke |
| 5,366,756 A | 11/1994 | Chesterfield et al. |
| 5,368,858 A | 11/1994 | Hunziker |
| 5,371,191 A | 12/1994 | Poser et al. |
| 5,376,375 A | 12/1994 | Rhee et al. |
| 5,393,739 A | 2/1995 | Bentz et al. |
| 5,397,572 A | 3/1995 | Coombes et al. |
| 5,399,361 A | 3/1995 | Song et al. |
| 5,405,390 A | 4/1995 | O'Leary et al. |
| 5,413,989 A | 5/1995 | Ogawa et al. |
| 5,417,975 A | 5/1995 | Lussi et al. |
| 5,422,340 A | 6/1995 | Ammann et al. |
| 5,425,770 A | 6/1995 | Piez et al. |
| 5,426,769 A | 6/1995 | Pawloski |
| 5,428,022 A | 6/1995 | Palefsky et al. |
| 5,433,751 A | 7/1995 | Christel et al. |
| 5,443,531 A | 8/1995 | Ripamonti |
| 5,455,231 A | 10/1995 | Constantz et al. |
| 5,466,462 A | 11/1995 | Rosenthal et al. |
| 5,475,052 A | 12/1995 | Rhee et al. |
| 5,484,601 A | 1/1996 | O'Leary et al. |
| 5,492,697 A | 2/1996 | Boyan et al. |
| 5,496,552 A | 3/1996 | Kuberasampath et al. |
| 5,507,813 A | 4/1996 | Dowd et al. |
| 5,508,267 A | 4/1996 | Czernuszka et al. |
| 5,510,396 A | 4/1996 | Prewett et al. |
| 5,522,893 A | 6/1996 | Chow et al. |
| 5,522,894 A | 6/1996 | Draenert |
| 5,531,791 A | 7/1996 | Wolfinbarger, Jr. |
| 5,532,217 A | 7/1996 | Silver et al. |
| 5,543,394 A | 8/1996 | Wozney et al. |
| 5,547,378 A | 8/1996 | Linkow |
| 5,549,671 A | 8/1996 | Waybright et al. |
| 5,552,454 A | 9/1996 | Kretschmann et al. |
| 5,563,124 A | 10/1996 | Damien et al. |
| 5,565,502 A | 10/1996 | Glimcher et al. |
| 5,573,771 A | 11/1996 | Geistlich et al. |
| 5,599,552 A | 2/1997 | Dunn et al. |
| 5,604,204 A | 2/1997 | Ammann et al. |
| 5,618,339 A | 4/1997 | Ito |
| 5,618,549 A | 4/1997 | Patat et al. |
| 5,639,402 A | 6/1997 | Barlow et al. |
| 5,645,591 A | 7/1997 | Kuberasampath et al. |
| 5,650,176 A | 7/1997 | Lee et al. |
| 5,661,007 A | 8/1997 | Wozney et al. |
| 5,670,483 A | 9/1997 | Zhang et al. |
| 5,674,290 A | 10/1997 | Li |
| 5,674,292 A | 10/1997 | Tucker et al. |
| 5,674,521 A | 10/1997 | Gehrke et al. |
| 5,676,146 A | 10/1997 | Scarborough |
| 5,676,699 A | 10/1997 | Gogolewski et al. |
| 5,677,284 A | 10/1997 | Li |
| 5,679,723 A | 10/1997 | Cooper et al. |
| 5,681,873 A | 10/1997 | Norton et al. |
| 5,683,459 A | 11/1997 | Brekke |
| 5,683,461 A | 11/1997 | Lee et al. |
| 5,686,425 A | 11/1997 | Lee |
| 5,691,397 A | 11/1997 | Glimcher et al. |
| RE35,694 E | 12/1997 | Seyedin et al. |
| 5,703,043 A | 12/1997 | Celeste et al. |

(56) References Cited

U.S. PATENT DOCUMENTS

| | | | |
|---|---|---|---|
| 5,707,442 A | 1/1998 | Fogel et al. |
| 5,707,962 A | 1/1998 | Chen et al. |
| 5,709,934 A | 1/1998 | Bell et al. |
| 5,711,957 A | 1/1998 | Patat et al. |
| 5,728,679 A | 3/1998 | Celeste et al. |
| 5,733,337 A | 3/1998 | Carr, Jr. et al. |
| 5,739,286 A | 4/1998 | Silver et al. |
| 5,741,329 A | 4/1998 | Agrawal et al. |
| 5,750,146 A | 5/1998 | Jones et al. |
| 5,755,792 A | 5/1998 | Brekke |
| 5,756,457 A | 5/1998 | Wang et al. |
| 5,769,895 A | 6/1998 | Ripamonti |
| 5,769,897 A | 6/1998 | Harle |
| 5,776,193 A | 7/1998 | Kwan et al. |
| 5,811,094 A | 9/1998 | Caplan et al. |
| 5,814,604 A | 9/1998 | Oppermann et al. |
| 5,824,084 A | 10/1998 | Muschler |
| 5,824,087 A | 10/1998 | Aspden et al. |
| 5,830,340 A | 11/1998 | Iljitch et al. |
| 5,830,493 A | 11/1998 | Yokota et al. |
| 5,837,752 A | 11/1998 | Shastri et al. |
| 5,840,325 A | 11/1998 | Kuberasampath et al. |
| 5,846,312 A | 12/1998 | Ison et al. |
| 5,854,207 A | 12/1998 | Lee et al. |
| 5,899,939 A | 5/1999 | Boyce et al. |
| 5,904,717 A | 5/1999 | Brekke et al. |
| 5,904,718 A | 5/1999 | Jefferies |
| 5,906,827 A | 5/1999 | Khouri et al. |
| 5,910,315 A | 6/1999 | Stevenson et al. |
| 5,910,492 A | 6/1999 | Hoshino et al. |
| 5,916,553 A | 6/1999 | Schmidt |
| 5,916,870 A | 6/1999 | Lee et al. |
| 5,919,408 A | 7/1999 | Muller et al. |
| 5,922,025 A | 7/1999 | Hubbard |
| 5,928,635 A | 7/1999 | Schmidt |
| 5,932,207 A | 8/1999 | Schmidt |
| 5,935,594 A | 8/1999 | Ringeisen et al. |
| 5,948,426 A | 9/1999 | Jefferies |
| 5,948,428 A | 9/1999 | Lee et al. |
| 5,948,429 A | 9/1999 | Bell et al. |
| 5,952,010 A | 9/1999 | Constantz |
| 5,955,438 A | 9/1999 | Pitaru et al. |
| 5,955,529 A | 9/1999 | Imai et al. |
| 5,958,430 A | 9/1999 | Campbell et al. |
| 5,958,441 A | 9/1999 | Oppermann et al. |
| 5,964,805 A | 10/1999 | Stone |
| 5,972,368 A | 10/1999 | McKay |
| 5,990,381 A | 11/1999 | Nishihara |
| 5,997,895 A | 12/1999 | Narotam et al. |
| 6,005,161 A | 12/1999 | Brekke et al. |
| 6,013,853 A | 1/2000 | Athanasiou et al. |
| 6,013,856 A | 1/2000 | Tucker et al. |
| 6,018,095 A | 1/2000 | Lerch et al. |
| 6,027,742 A | 2/2000 | Lee et al. |
| 6,027,743 A | 2/2000 | Khouri et al. |
| 6,028,242 A | 2/2000 | Tucker et al. |
| 6,033,438 A | 3/2000 | Bianchi et al. |
| 6,037,519 A | 3/2000 | McKay |
| 6,039,762 A | 3/2000 | McKay |
| 6,048,964 A | 4/2000 | Lee et al. |
| 6,071,982 A | 6/2000 | Wise et al. |
| 6,077,988 A | 6/2000 | Kuberasampath et al. |
| 6,090,996 A | 7/2000 | Li |
| 6,110,482 A | 8/2000 | Khouri et al. |
| 6,118,043 A | 9/2000 | Nies et al. |
| 6,123,731 A | 9/2000 | Boyce et al. |
| 6,123,957 A | 9/2000 | Jernberg |
| 6,132,463 A | 10/2000 | Lee et al. |
| 6,132,468 A | 10/2000 | Mansmann |
| 6,136,029 A | 10/2000 | Johnson et al. |
| 6,136,030 A | 10/2000 | Lin et al. |
| 6,139,578 A | 10/2000 | Lee et al. |
| 6,165,487 A | 12/2000 | Ashkar et al. |
| 6,168,801 B1 | 1/2001 | Heil, Jr. et al. |
| 6,177,406 B1 | 1/2001 | Wang et al. |
| 6,180,605 B1 | 1/2001 | Chen et al. |
| 6,180,606 B1 | 1/2001 | Chen et al. |
| 6,183,515 B1 | 2/2001 | Barlow et al. |
| 6,183,737 B1 | 2/2001 | Zaleske et al. |
| 6,187,046 B1 | 2/2001 | Yamamoto et al. |
| 6,187,047 B1 | 2/2001 | Kwan et al. |
| 6,187,329 B1 | 2/2001 | Agrawal et al. |
| 6,187,742 B1 | 2/2001 | Wozney et al. |
| 6,189,537 B1 | 2/2001 | Wolfinbarger, Jr. |
| 6,201,039 B1 | 3/2001 | Brown et al. |
| 6,203,573 B1 | 3/2001 | Walter et al. |
| 6,203,574 B1 | 3/2001 | Kawamura |
| 6,206,924 B1 | 3/2001 | Timm |
| 6,206,931 B1 | 3/2001 | Cook et al. |
| 6,214,049 B1 | 4/2001 | Gayer et al. |
| 6,214,368 B1 | 4/2001 | Lee et al. |
| 6,221,109 B1 | 4/2001 | Geistlich et al. |
| 6,241,771 B1 | 6/2001 | Gresser et al. |
| 6,261,565 B1 | 7/2001 | Empie et al. |
| 6,261,586 B1 | 7/2001 | McKay |
| 6,264,701 B1 | 7/2001 | Brekke |
| 6,277,151 B1 | 8/2001 | Lee et al. |
| 6,280,191 B1 | 8/2001 | Gordon |
| 6,280,474 B1 | 8/2001 | Cassidy et al. |
| 6,281,195 B1 | 8/2001 | Rueger et al. |
| 6,287,341 B1 | 9/2001 | Lee et al. |
| 6,287,816 B1 | 9/2001 | Rosen et al. |
| 6,294,041 B1 | 9/2001 | Boyce et al. |
| 6,294,187 B1 | 9/2001 | Boyce et al. |
| 6,296,667 B1 | 10/2001 | Johnson et al. |
| 6,297,213 B1 | 10/2001 | Oppermann et al. |
| 6,299,650 B1 | 10/2001 | Van Blitterswijk et al. |
| 6,300,315 B1 | 10/2001 | Liu |
| 6,302,913 B1 | 10/2001 | Ripamonti et al. |
| 6,306,169 B1 | 10/2001 | Lee et al. |
| 6,309,422 B1 | 10/2001 | Farrington et al. |
| 6,309,909 B1 | 10/2001 | Ohgiyama |
| 6,311,690 B1 | 11/2001 | Jefferies |
| 6,326,018 B1 | 12/2001 | Gertzman et al. |
| 6,331,312 B1 | 12/2001 | Lee et al. |
| 6,335,007 B1 | 1/2002 | Shimizu et al. |
| 6,340,648 B1 | 1/2002 | Imura et al. |
| 6,346,123 B1 | 2/2002 | McKay |
| 6,352,972 B1 | 3/2002 | Nimni et al. |
| 6,371,985 B1 | 4/2002 | Goldberg |
| 6,372,257 B1 | 4/2002 | Marchosky |
| 6,376,211 B1 | 4/2002 | Little, II et al. |
| 6,379,385 B1 | 4/2002 | Kalas et al. |
| 6,383,519 B1 | 5/2002 | Sapieszko et al. |
| 6,384,196 B1 | 5/2002 | Weis et al. |
| 6,384,197 B1 * | 5/2002 | Weis et al. ............... 530/356 |
| 6,395,036 B1 | 5/2002 | Czernuszka et al. |
| 6,406,498 B1 | 6/2002 | Tormala et al. |
| 6,417,166 B2 | 7/2002 | Liu |
| 6,419,708 B1 | 7/2002 | Hall et al. |
| 6,423,095 B1 | 7/2002 | Van Hoeck et al. |
| 6,425,949 B1 | 7/2002 | Lemaitre et al. |
| 6,426,332 B1 | 7/2002 | Rueger et al. |
| 6,432,919 B1 | 8/2002 | Wang et al. |
| 6,440,444 B2 | 8/2002 | Boyce et al. |
| 6,444,222 B1 | 9/2002 | Asculai et al. |
| 6,454,787 B1 | 9/2002 | Maddalo et al. |
| 6,461,630 B1 | 10/2002 | Tucker et al. |
| 6,468,308 B1 | 10/2002 | Kuberasampath et al. |
| 6,471,993 B1 | 10/2002 | Shastri et al. |
| 6,478,825 B1 | 11/2002 | Winterbottom et al. |
| 6,479,065 B2 | 11/2002 | Jaworowicz et al. |
| 6,479,565 B1 | 11/2002 | Stanley |
| 6,504,079 B2 | 1/2003 | Tucker et al. |
| 6,506,217 B1 | 1/2003 | Arnett |
| 6,511,510 B1 | 1/2003 | de Bruijn et al. |
| 6,511,958 B1 | 1/2003 | Atkinson et al. |
| 6,514,514 B1 | 2/2003 | Atkinson et al. |
| 6,521,246 B2 | 2/2003 | Sapieszko et al. |
| 6,524,345 B1 | 2/2003 | Valimaa et al. |
| 6,540,784 B2 | 4/2003 | Barlow et al. |
| 6,541,023 B1 | 4/2003 | Andre et al. |
| 6,544,290 B1 | 4/2003 | Lee et al. |
| 6,547,866 B1 | 4/2003 | Edwards et al. |

(56) References Cited

U.S. PATENT DOCUMENTS

| | | |
|---|---|---|
| 6,548,002 B2 | 4/2003 | Gresser et al. |
| 6,551,355 B1 | 4/2003 | Lewandrowski et al. |
| 6,551,995 B1 | 4/2003 | Oppermann et al. |
| 6,576,015 B2 | 6/2003 | Geistlich et al. |
| 6,576,249 B1 | 6/2003 | Gendler et al. |
| 6,582,471 B1 | 6/2003 | Bittmann et al. |
| 6,589,590 B2 | 7/2003 | Czernuszka et al. |
| 6,602,294 B1 | 8/2003 | Sittinger et al. |
| 6,645,250 B2 | 11/2003 | Schulter |
| 6,679,918 B1 | 1/2004 | Benedict et al. |
| 6,696,073 B2 | 2/2004 | Boyce et al. |
| 6,712,822 B2 | 3/2004 | Re et al. |
| 6,736,799 B1 | 5/2004 | Erbe et al. |
| 6,764,517 B2 | 7/2004 | Yamamoto et al. |
| 6,840,961 B2 | 1/2005 | Tofighi et al. |
| 6,846,327 B2 | 1/2005 | Khandkar et al. |
| 6,884,621 B2 | 4/2005 | Liao et al. |
| 6,899,107 B2 | 5/2005 | Lewandrowski et al. |
| 6,902,584 B2 | 6/2005 | Kwan et al. |
| 6,903,146 B2 | 6/2005 | Matsushima et al. |
| 6,911,046 B2 | 6/2005 | Schulter |
| 6,911,212 B2 | 6/2005 | Gertzman et al. |
| 6,921,412 B1 | 7/2005 | Black et al. |
| 6,933,326 B1 | 8/2005 | Griffey et al. |
| 6,953,594 B2 | 10/2005 | Lee et al. |
| 6,974,862 B2 | 12/2005 | Ringeisen et al. |
| 6,991,803 B2 | 1/2006 | Sapieszko et al. |
| 7,026,292 B1 | 4/2006 | Lee et al. |
| 7,045,141 B2 | 5/2006 | Merboth et al. |
| 7,052,517 B2 | 5/2006 | Murphy et al. |
| 7,077,866 B2 | 7/2006 | Gresser et al. |
| 7,105,182 B2 | 9/2006 | Szymaitis |
| 7,122,057 B2 | 10/2006 | Beam et al. |
| 7,132,110 B2 | 11/2006 | Kay et al. |
| 7,153,938 B2 | 12/2006 | Kikuchi et al. |
| 7,156,880 B2 | 1/2007 | Evans et al. |
| 7,163,691 B2 | 1/2007 | Knaack et al. |
| 7,163,965 B2 | 1/2007 | Sotome et al. |
| 7,166,133 B2 | 1/2007 | Evans et al. |
| 7,172,629 B2 | 2/2007 | McKay |
| 7,175,858 B2 | 2/2007 | Constantz et al. |
| 7,189,263 B2 | 3/2007 | Erbe et al. |
| 7,189,392 B1 | 3/2007 | Kim et al. |
| 7,229,545 B2 | 6/2007 | Sewing et al. |
| 7,235,107 B2 | 6/2007 | Evans et al. |
| 7,241,316 B2 | 7/2007 | Evans et al. |
| 7,250,550 B2 | 7/2007 | Overby et al. |
| 7,252,685 B2 | 8/2007 | Bindseil et al. |
| 7,252,841 B2 | 8/2007 | Constantz et al. |
| 7,303,814 B2 | 12/2007 | Lamberti et al. |
| 7,318,840 B2 | 1/2008 | McKay |
| 7,318,841 B2 | 1/2008 | Tofighi et al. |
| 7,358,284 B2 | 4/2008 | Griffey et al. |
| 7,473,678 B2 | 1/2009 | Lynch |
| 7,485,617 B1 | 2/2009 | Pohl et al. |
| 7,494,950 B2 | 2/2009 | Armitage et al. |
| 7,498,040 B2 | 3/2009 | Masinaei et al. |
| 7,498,041 B2 | 3/2009 | Masinaei et al. |
| 7,517,539 B1 | 4/2009 | Lee et al. |
| 7,531,004 B2 | 5/2009 | Bagga et al. |
| 7,534,264 B2 | 5/2009 | Fischer |
| 7,534,451 B2 | 5/2009 | Erbe et al. |
| 7,621,963 B2 | 11/2009 | Simon et al. |
| 7,628,851 B2 | 12/2009 | Armitage et al. |
| 7,670,378 B2 | 3/2010 | Bloemer et al. |
| 7,670,384 B2 | 3/2010 | Kimar et al. |
| 7,686,239 B2 | 3/2010 | Tofighi et al. |
| 7,718,616 B2 * | 5/2010 | Thorne ........................ 514/17.2 |
| 7,722,895 B1 | 5/2010 | McKay et al. |
| 7,771,741 B2 | 8/2010 | Drapeau et al. |
| 7,776,100 B2 | 8/2010 | Brekke et al. |
| 7,780,994 B2 | 8/2010 | Lynn et al. |
| 7,785,617 B2 | 8/2010 | Shakesheff et al. |
| 7,799,767 B2 | 9/2010 | Lamberti et al. |
| 7,811,608 B2 | 10/2010 | Kay et al. |
| 7,824,702 B2 | 11/2010 | Wironen et al. |
| 7,833,278 B2 | 11/2010 | Evans et al. |
| 7,857,860 B2 | 12/2010 | Saini et al. |
| 7,887,598 B2 | 2/2011 | Evans et al. |
| 7,887,831 B2 | 2/2011 | Yayon |
| 7,892,291 B2 | 2/2011 | Evans et al. |
| 7,897,722 B2 | 3/2011 | Chung et al. |
| 7,910,690 B2 | 3/2011 | Ringeisen et al. |
| 7,951,200 B2 | 5/2011 | Heinz |
| 7,959,941 B2 | 6/2011 | Knaack et al. |
| 7,963,997 B2 | 6/2011 | Brekke et al. |
| 8,029,575 B2 | 10/2011 | Borden |
| 8,497,236 B2 | 7/2013 | Benedict et al. |
| 2001/0004225 A1 | 6/2001 | Nicholls et al. |
| 2001/0005797 A1 | 6/2001 | Barlow et al. |
| 2001/0008980 A1 | 7/2001 | Gresser et al. |
| 2001/0010023 A1 | 7/2001 | Schwartz et al. |
| 2001/0012968 A1 | 8/2001 | Preissman |
| 2001/0014662 A1 | 8/2001 | Rueger et al. |
| 2001/0014667 A1 | 8/2001 | Chen et al. |
| 2001/0014830 A1 | 8/2001 | Kwan et al. |
| 2001/0014831 A1 | 8/2001 | Scarborough |
| 2001/0016646 A1 | 8/2001 | Rueger et al. |
| 2001/0016772 A1 | 8/2001 | Lee et al. |
| 2001/0018614 A1 | 8/2001 | Bianchi |
| 2001/0018797 A1 | 9/2001 | Shepherd |
| 2001/0020476 A1 | 9/2001 | Gan et al. |
| 2001/0031799 A1 | 10/2001 | Shimp |
| 2001/0037014 A1 | 11/2001 | Liu |
| 2001/0039453 A1 | 11/2001 | Gresser et al. |
| 2001/0041792 A1 | 11/2001 | Donda et al. |
| 2001/0041942 A1 | 11/2001 | Ylanen et al. |
| 2001/0043940 A1 | 11/2001 | Boyce et al. |
| 2001/0044413 A1 | 11/2001 | Pierce et al. |
| 2001/0049141 A1 | 12/2001 | Fike et al. |
| 2001/0051834 A1 | 12/2001 | Frondoza et al. |
| 2001/0053937 A1 | 12/2001 | Johnson et al. |
| 2001/0055622 A1 | 12/2001 | Burrell et al. |
| 2002/0013626 A1 | 1/2002 | Geistlich et al. |
| 2002/0013627 A1 | 1/2002 | Geistlich et al. |
| 2002/0018796 A1 | 2/2002 | Wironen |
| 2002/0018797 A1 | 2/2002 | Cui et al. |
| 2002/0018798 A1 | 2/2002 | Sewing et al. |
| 2002/0022883 A1 | 2/2002 | Burg |
| 2002/0022885 A1 | 2/2002 | Ochi |
| 2002/0034532 A1 | 3/2002 | Brodbeck et al. |
| 2002/0034533 A1 | 3/2002 | Peterson et al. |
| 2002/0037309 A1 | 3/2002 | Jaworowicz et al. |
| 2002/0042657 A1 | 4/2002 | Pugh et al. |
| 2002/0045582 A1 | 4/2002 | Margolin et al. |
| 2002/0053937 A1 | 5/2002 | Lloyd |
| 2002/0054901 A1 | 5/2002 | Gainey et al. |
| 2002/0055143 A1 | 5/2002 | Bell et al. |
| 2002/0058622 A1 | 5/2002 | Igari et al. |
| 2002/0061328 A1 | 5/2002 | Gertzman et al. |
| 2002/0072804 A1 | 6/2002 | Donda |
| 2002/0076429 A1 | 6/2002 | Wironen et al. |
| 2002/0082220 A1 | 6/2002 | Hoemann et al. |
| 2002/0082594 A1 | 6/2002 | Hata et al. |
| 2002/0082694 A1 | 6/2002 | McKay |
| 2002/0082697 A1 | 6/2002 | Damien |
| 2002/0082700 A1 | 6/2002 | Bianchi et al. |
| 2002/0090725 A1 | 7/2002 | Simpson et al. |
| 2002/0098222 A1 | 7/2002 | Wironen et al. |
| 2002/0106393 A1 | 8/2002 | Bianchi et al. |
| 2002/0106394 A1 | 8/2002 | Tucker et al. |
| 2002/0114795 A1 | 8/2002 | Thorne et al. |
| 2002/0128722 A1 | 9/2002 | Jefferies |
| 2002/0192263 A1 | 12/2002 | Merboth et al. |
| 2003/0009235 A1 | 1/2003 | Manrique et al. |
| 2003/0036797 A1 | 2/2003 | Malaviya et al. |
| 2003/0143207 A1 | 7/2003 | Livesey et al. |
| 2003/0152606 A1 | 8/2003 | Gerber |
| 2003/0232071 A1 | 12/2003 | Gower et al. |
| 2003/0236573 A1 | 12/2003 | Evans et al. |
| 2004/0002558 A1 | 1/2004 | McKay |
| 2004/0062816 A1 | 4/2004 | Atkinson et al. |
| 2004/0081704 A1 | 4/2004 | Benedict et al. |
| 2004/0131562 A1 | 7/2004 | Gower et al. |

(56) References Cited

U.S. PATENT DOCUMENTS

| | | |
|---|---|---|
| 2004/0181232 A1 | 9/2004 | Re et al. |
| 2004/0197311 A1 | 10/2004 | Brekke et al. |
| 2004/0220680 A1 | 11/2004 | Yamamoto et al. |
| 2005/0053638 A1 | 3/2005 | Tanaka et al. |
| 2005/0079201 A1 | 4/2005 | Rathenow et al. |
| 2005/0089579 A1 | 4/2005 | Li et al. |
| 2005/0199156 A1 | 9/2005 | Khairoun et al. |
| 2005/0217538 A1 | 10/2005 | Reinstorf et al. |
| 2005/0249773 A1 | 11/2005 | Maspero et al. |
| 2005/0251266 A1 | 11/2005 | Maspero et al. |
| 2005/0261767 A1 | 11/2005 | Anderson et al. |
| 2005/0283255 A1 | 12/2005 | Geremakis et al. |
| 2005/0288795 A1 | 12/2005 | Bagga et al. |
| 2006/0030627 A1 | 2/2006 | Yamamoto et al. |
| 2006/0030948 A1 | 2/2006 | Manrique et al. |
| 2006/0039951 A1 | 2/2006 | Sapieszko et al. |
| 2006/0093670 A1 | 5/2006 | Mizushima et al. |
| 2006/0147547 A1 | 7/2006 | Yayon |
| 2006/0184131 A1 | 8/2006 | Murphy et al. |
| 2006/0204544 A1 | 9/2006 | Sunwoo et al. |
| 2006/0204580 A1 | 9/2006 | Gower et al. |
| 2006/0204581 A1 | 9/2006 | Gower et al. |
| 2006/0216321 A1 | 9/2006 | Lyu et al. |
| 2006/0233851 A1 | 10/2006 | Simon et al. |
| 2006/0246150 A1 | 11/2006 | Thorne |
| 2006/0251729 A1 | 11/2006 | Kay et al. |
| 2006/0270037 A1 | 11/2006 | Kato et al. |
| 2006/0292350 A1 | 12/2006 | Kawamura et al. |
| 2007/0003593 A1 | 1/2007 | Wironen et al. |
| 2007/0071791 A1 | 3/2007 | Fischer |
| 2007/0088437 A1 | 4/2007 | Betz et al. |
| 2007/0093912 A1 | 4/2007 | Borden |
| 2007/0128249 A1 | 6/2007 | McKay |
| 2007/0129807 A1 | 6/2007 | Lynch et al. |
| 2007/0134285 A1 | 6/2007 | Lynn et al. |
| 2007/0154563 A1 | 7/2007 | Behnam et al. |
| 2007/0178158 A1 | 8/2007 | Knaack et al. |
| 2007/0191963 A1 | 8/2007 | Winterbottom et al. |
| 2007/0202148 A1 | 8/2007 | Ringeisen et al. |
| 2007/0231788 A1 | 10/2007 | Behnam et al. |
| 2007/0233272 A1 | 10/2007 | Boyce et al. |
| 2007/0248575 A1 | 10/2007 | Connor et al. |
| 2007/0276489 A1 | 11/2007 | Bindseil et al. |
| 2008/0015692 A1 | 1/2008 | Heinz |
| 2008/0015709 A1 | 1/2008 | Evans et al. |
| 2008/0033548 A1 | 2/2008 | Xuenong et al. |
| 2008/0033572 A1 | 2/2008 | D'Antonio et al. |
| 2008/0063671 A1 | 3/2008 | Morris et al. |
| 2008/0065210 A1 | 3/2008 | McKay |
| 2008/0069852 A1 | 3/2008 | Shimp et al. |
| 2008/0095815 A1 | 4/2008 | Mao |
| 2008/0114458 A1 | 5/2008 | McKay |
| 2008/0124397 A1 | 5/2008 | Wironen et al. |
| 2008/0145392 A1 | 6/2008 | Knaack et al. |
| 2008/0145404 A1 | 6/2008 | Hill et al. |
| 2008/0147065 A1 | 6/2008 | McKay et al. |
| 2008/0147197 A1 | 6/2008 | McKay |
| 2008/0152687 A1 | 6/2008 | Thorne |
| 2008/0188945 A1 | 8/2008 | Boyce et al. |
| 2008/0188946 A1 | 8/2008 | Rosenberg et al. |
| 2008/0199508 A1 | 8/2008 | Lamberti et al. |
| 2008/0233203 A1 | 9/2008 | Woodell-May et al. |
| 2008/0241211 A1 | 10/2008 | Han |
| 2008/0249637 A1 | 10/2008 | Asgari et al. |
| 2008/0262613 A1 | 10/2008 | Gogolewski |
| 2008/0293617 A1 | 11/2008 | Benedict et al. |
| 2008/0317817 A1 | 12/2008 | Fischer |
| 2009/0012625 A1 | 1/2009 | Ying et al. |
| 2009/0017093 A1 | 1/2009 | Springer et al. |
| 2009/0123547 A1 | 5/2009 | Hill et al. |
| 2009/0124552 A1 | 5/2009 | Hill et al. |
| 2009/0142385 A1 | 6/2009 | Gross et al. |
| 2009/0148495 A1 | 6/2009 | Hammer et al. |
| 2009/0155366 A1 | 6/2009 | Pohl et al. |
| 2009/0157182 A1 | 6/2009 | Koblish et al. |
| 2009/0246244 A1 | 10/2009 | McKay et al. |
| 2009/0254104 A1 | 10/2009 | Murray |
| 2009/0269388 A1 | 10/2009 | Sunwoo et al. |
| 2009/0292359 A1 | 11/2009 | Borden |
| 2009/0292360 A1 | 11/2009 | Borden |
| 2009/0292367 A1 | 11/2009 | Borden |
| 2009/0324675 A1 | 12/2009 | Gunatillake et al. |
| 2010/0004733 A1 | 1/2010 | Atanasoska et al. |
| 2010/0015230 A1 | 1/2010 | Ron |
| 2010/0021520 A1 | 1/2010 | Baskin et al. |
| 2010/0036503 A1 | 2/2010 | Chen et al. |
| 2010/0048763 A1 | 2/2010 | Armitage et al. |
| 2010/0049322 A1 | 2/2010 | McKay |
| 2010/0049330 A1 | 2/2010 | Horvath |
| 2010/0082072 A1 | 4/2010 | Sybert et al. |
| 2010/0098673 A1 | 4/2010 | D'Antonnio et al. |
| 2010/0131074 A1 | 5/2010 | Shikinami |
| 2010/0168869 A1 | 7/2010 | Long et al. |
| 2010/0209408 A1 | 8/2010 | Stephen A. |
| 2010/0209470 A1 | 8/2010 | Mohan et al. |
| 2010/0226961 A1 | 9/2010 | Lamberti et al. |
| 2010/0255115 A1 | 10/2010 | Mohan et al. |
| 2010/0266658 A1 | 10/2010 | McKay et al. |
| 2010/0266660 A1 | 10/2010 | McKay et al. |
| 2010/0268227 A1 | 10/2010 | Tong et al. |
| 2011/0045044 A1 | 2/2011 | Masinaei et al. |
| 2011/0133368 A1 | 6/2011 | Ringeisen et al. |
| 2011/0140137 A1 | 6/2011 | Lai |
| 2011/0144767 A1 | 6/2011 | Evans et al. |
| 2011/0165199 A1 | 7/2011 | Thorne et al. |
| 2011/0183936 A1 | 7/2011 | Bailleul |
| 2012/0121660 A1 | 5/2012 | Akella et al. |

FOREIGN PATENT DOCUMENTS

| | | |
|---|---|---|
| CA | 2 446 840 A1 | 7/2002 |
| CA | 2280966 C | 4/2012 |
| CN | 103313733 A | 9/2013 |
| EP | 0164483 A1 | 12/1985 |
| EP | 0171176 A2 | 2/1986 |
| EP | 0197693 A2 | 10/1986 |
| EP | 0233770 A2 | 8/1987 |
| EP | 0243178 A2 | 10/1987 |
| EP | 0271668 A1 | 6/1988 |
| EP | 289562 A1 | 11/1988 |
| EP | 309241 A2 | 3/1989 |
| EP | 321277 A2 | 6/1989 |
| EP | 0 349 048 A2 | 1/1990 |
| EP | 0361896 A2 | 4/1990 |
| EP | 0243178 B1 | 6/1991 |
| EP | 0197693 B1 | 10/1991 |
| EP | 271668 B1 | 12/1991 |
| EP | 321277 B1 | 3/1992 |
| EP | 0522569 A1 | 1/1993 |
| EP | 522569 A1 | 1/1993 |
| EP | 289562 B1 | 2/1993 |
| EP | 0270254 B1 | 3/1993 |
| EP | 0558727 A1 | 9/1993 |
| EP | 0567391 A1 | 10/1993 |
| EP | 309241 B1 | 12/1993 |
| EP | 0309241 B1 | 12/1993 |
| EP | 573491 A1 | 12/1993 |
| EP | 0446262 B1 | 3/1994 |
| EP | 0588727 A1 | 3/1994 |
| EP | 0605799 A1 | 7/1994 |
| EP | 0605933 B1 | 7/1994 |
| EP | 608313 A1 | 8/1994 |
| EP | 0621044 A2 | 10/1994 |
| EP | 0668478 B1 | 10/1994 |
| EP | 0623031 A1 | 11/1994 |
| EP | 0439689 B1 | 12/1994 |
| EP | 627899 A1 | 12/1994 |
| EP | 0674908 A1 | 10/1995 |
| EP | 0719529 A1 | 7/1996 |
| EP | 0429438 B1 | 8/1996 |
| EP | 732947 A1 | 9/1996 |
| EP | 0747067 A2 | 12/1996 |
| EP | 0754699 A1 | 1/1997 |
| EP | 855884 B1 | 4/1997 |

(56) References Cited

FOREIGN PATENT DOCUMENTS

| | | | |
|---|---|---|---|
| EP | 828453 | A1 | 3/1998 |
| EP | 837701 | A1 | 4/1998 |
| EP | 855884 | A1 | 8/1998 |
| EP | 0588727 | B1 | 11/1998 |
| EP | 0901795 | A2 | 3/1999 |
| EP | 0605799 | B1 | 4/1999 |
| EP | 0932373 | A1 | 8/1999 |
| EP | 1795214 | A2 | 8/1999 |
| EP | 608313 | B1 | 2/2000 |
| EP | 0623031 | B1 | 2/2000 |
| EP | 0987031 | A1 | 3/2000 |
| EP | 1019027 | A1 | 7/2000 |
| EP | 1053739 | A1 | 11/2000 |
| EP | 1120439 | A1 | 8/2001 |
| EP | 1127581 | A1 | 8/2001 |
| EP | 627899 | B1 | 11/2001 |
| EP | 1150659 | | 11/2001 |
| EP | 1150725 | A1 | 11/2001 |
| EP | 1150726 | A1 | 11/2001 |
| EP | 1178769 | A1 | 2/2002 |
| EP | 1180986 | A2 | 2/2002 |
| EP | 732947 | B1 | 3/2002 |
| EP | 573491 | B1 | 4/2002 |
| EP | 1224925 | A2 | 7/2002 |
| EP | 1233714 | A1 | 8/2002 |
| EP | 1234587 | A1 | 8/2002 |
| EP | 0719529 | B1 | 9/2002 |
| EP | 837701 | B1 | 2/2003 |
| EP | 0987031 | B1 | 4/2003 |
| EP | 1434608 | A2 | 4/2003 |
| EP | 1150726 | B1 | 11/2003 |
| EP | 1019027 | A4 | 5/2004 |
| EP | 1416977 | A2 | 5/2004 |
| EP | 1419791 | A1 | 5/2004 |
| EP | 0855884 | B1 | 6/2004 |
| EP | 1120439 | B1 | 6/2004 |
| EP | 1425024 | A2 | 6/2004 |
| EP | 1437148 | A1 | 7/2004 |
| EP | 1462126 | A1 | 9/2004 |
| EP | 1476202 | A1 | 11/2004 |
| EP | 1476204 | A1 | 11/2004 |
| EP | 1482872 | A1 | 12/2004 |
| EP | 1500405 | A1 | 1/2005 |
| EP | 1677846 | | 5/2005 |
| EP | 1150725 | B1 | 6/2005 |
| EP | 1545466 | A1 | 6/2005 |
| EP | 1701672 | | 7/2005 |
| EP | 1701729 | | 7/2005 |
| EP | 1 561 480 | A2 | 8/2005 |
| EP | 1708651 | A1 | 8/2005 |
| EP | 1727489 | A2 | 8/2005 |
| EP | 828453 | B1 | 11/2005 |
| EP | 1234587 | B1 | 11/2005 |
| EP | 1608414 | A2 | 12/2005 |
| EP | 1623681 | A1 | 2/2006 |
| EP | 1638486 | A2 | 3/2006 |
| EP | 1642599 | A1 | 4/2006 |
| EP | 1648347 | | 4/2006 |
| EP | 1178769 | B1 | 7/2006 |
| EP | 1712244 | A1 | 10/2006 |
| EP | 1727489 | A1 | 12/2006 |
| EP | 1753474 | A2 | 2/2007 |
| EP | 1771490 | A1 | 4/2007 |
| EP | 1940313 | | 5/2007 |
| EP | 1976459 | | 7/2007 |
| EP | 1976460 | | 7/2007 |
| EP | 0616814 | A1 | 10/2007 |
| EP | 1839622 | A2 | 10/2007 |
| EP | 1844798 | A1 | 10/2007 |
| EP | 2007196 | | 11/2007 |
| EP | 1925325 | A1 | 5/2008 |
| EP | 1608414 | B1 | 7/2008 |
| EP | 2125055 | | 9/2008 |
| EP | 1476204 | B1 | 10/2008 |
| EP | 2139500 | | 10/2008 |
| EP | 1476202 | B1 | 1/2009 |
| EP | 2049591 | A1 | 4/2009 |
| EP | 2070491 | A2 | 6/2009 |
| EP | 2104518 | A2 | 9/2009 |
| EP | 1464345 | B1 | 12/2009 |
| EP | 2129318 | A2 | 12/2009 |
| EP | 1419791 | B1 | 2/2010 |
| EP | 1416977 | B1 | 7/2010 |
| EP | 2260790 | A2 | 12/2010 |
| EP | 1233714 | B1 | 2/2012 |
| GB | 1224925 | | 3/1971 |
| GB | 2164042 | A | 3/1986 |
| GB | 2 377 642 | | 5/2001 |
| JP | 61226055 | A | 10/1986 |
| JP | 63066106 | A | 3/1988 |
| JP | 1076861 | | 3/1989 |
| JP | 64076861 | | 3/1989 |
| JP | 1121059 | A | 5/1989 |
| JP | 01121059 | A | 5/1989 |
| JP | 1250264 | A | 10/1989 |
| JP | 06100410 | | 4/1994 |
| JP | 6100410 | | 4/1994 |
| JP | 8505548 | A | 6/1996 |
| JP | 9505305 | | 5/1997 |
| JP | 11164880 | A | 6/1999 |
| JP | 11506727 | A | 6/1999 |
| JP | 11313882 | A | 11/1999 |
| JP | 11313883 | A | 11/1999 |
| JP | 2000262608 | A | 9/2000 |
| JP | 2002501786 | A | 1/2002 |
| JP | 2004520106 | A | 7/2004 |
| JP | 5105216 | A | 10/2012 |
| WO | WO-8707495 | A1 | 12/1987 |
| WO | WO 89/04646 | | 6/1989 |
| WO | WO-9000892 | A1 | 2/1990 |
| WO | WO-9200109 | A1 | 1/1992 |
| WO | WO-9209697 | A1 | 6/1992 |
| WO | WO-9305823 | A1 | 4/1993 |
| WO | WO-9312736 | A1 | 7/1993 |
| WO | WO-9313815 | A1 | 7/1993 |
| WO | WO-9316739 | A1 | 9/1993 |
| WO | WO-9320857 | A1 | 10/1993 |
| WO | WO-9402412 | A1 | 2/1994 |
| WO | WO-9415653 | A1 | 7/1994 |
| WO | WO-9420064 | A1 | 9/1994 |
| WO | WO-9525550 | A1 | 9/1995 |
| WO | WO-9610374 | A1 | 4/1996 |
| WO | WO-9610428 | A1 | 4/1996 |
| WO | WO-9639203 | A1 | 12/1996 |
| WO | WO-9640297 | A1 | 12/1996 |
| WO | WO-9817330 | A1 | 4/1998 |
| WO | WO-9830141 | A2 | 7/1998 |
| WO | WO-9835653 | A1 | 8/1998 |
| WO | WO-9840113 | A1 | 9/1998 |
| WO | WO-9851354 | A2 | 11/1998 |
| WO | WO-9858602 | A1 | 12/1998 |
| WO | WO-9915211 | A1 | 4/1999 |
| WO | WO-9919003 | A1 | 4/1999 |
| WO | WO-0004940 | A1 | 2/2000 |
| WO | WO-0032251 | A1 | 6/2000 |
| WO | WO-0045870 | A1 | 8/2000 |
| WO | WO-0045871 | A1 | 8/2000 |
| WO | WO-0047114 | A1 | 8/2000 |
| WO | WO-0071178 | A1 | 11/2000 |
| WO | WO-0074690 | A1 | 12/2000 |
| WO | WO-0130409 | A1 | 5/2001 |
| WO | WO-0132072 | A2 | 5/2001 |
| WO | WO-0141821 | A1 | 6/2001 |
| WO | WO-0141822 | A1 | 6/2001 |
| WO | WO-0166044 | A2 | 9/2001 |
| WO | WO-0174410 | A1 | 10/2001 |
| WO | WO-0207961 | A1 | 1/2002 |
| WO | WO-0211781 | A1 | 2/2002 |
| WO | WO-0221222 | A1 | 3/2002 |
| WO | WO-0222045 | A1 | 3/2002 |
| WO | WO-0224107 | A2 | 3/2002 |
| WO | WO-0234113 | A2 | 5/2002 |
| WO | WO-0234116 | A2 | 5/2002 |
| WO | WO-0240073 | A1 | 5/2002 |

(56) References Cited

FOREIGN PATENT DOCUMENTS

| WO | WO-0240963 A2 | 5/2002 |
|---|---|---|
| WO | WO 2002/051449 A2 | 7/2002 |
| WO | WO-02051449 A3 | 7/2002 |
| WO | WO-02070029 A2 | 9/2002 |
| WO | WO 2003/071991 A1 | 9/2003 |
| WO | WO-03092759 A1 | 11/2003 |
| WO | WO-2004078120 A2 | 9/2004 |
| WO | WO-2004091435 A2 | 10/2004 |
| WO | WO-2004103422 A1 | 12/2004 |
| WO | WO 2005/004755 A1 | 1/2005 |
| WO | WO-2005051447 A1 | 6/2005 |
| WO | WO 2005/074614 A2 | 8/2005 |
| WO | WO-2005081699 A2 | 9/2005 |
| WO | WO-2005099785 A1 | 10/2005 |
| WO | WO-2006031196 A1 | 3/2006 |
| WO | WO-2006092718 A2 | 9/2006 |
| WO | WO-2007053850 A2 | 5/2007 |
| WO | WO-2008019024 A2 | 2/2008 |
| WO | WO-2008076604 A1 | 6/2008 |
| WO | WO-2009052967 A1 | 4/2009 |
| WO | WO-2010117766 A1 | 10/2010 |
| WO | WO-2010119476 A2 | 10/2010 |
| WO | WO-2010134102 A1 | 11/2010 |
| WO | WO-2012068135 A1 | 5/2012 |

OTHER PUBLICATIONS

"Tri-Calcium Phosphates as a Biomaterial", [Online]. Retrieved from the Internet: <URL: http://www.scribd.com/doc/56970573/Tri-Calcium-Phosphates-as-a-Biomaterial>, (Upload Date: Jun. 2, 2011), 5 pgs.
Chakkalakal, D A, et al., "Mineralization and pH relationships in healing skeletal defects grafted with demineralized bone matrix", Journal of Biomedical Materials Research vol. 28,, (1994), 1439-1443.
Clarke, K. I., et al., "Investigation into the Formation and Mechanical Properties of a Bioactive Material Based on Collagen and Calcium Phosphate", Journal of Materials Science in Medicine, 4, (1993), 107-110.
Donlon, William, "Immune Neutrality of Calf Skin Collagen Gel Used to Stimulate Revitalization in Pulpless Open Apex Teeth of Rhesus Monkeys", J Dent Res, (Jun. 1977), 670-673.
Kohles, S S, et al., "A Morphometric Evaluation of Allograft Matrix Combinations in the Treatment of Osseous Defects in a Baboon Model", Calcif. Tissue Int. 67, (2000), 156-162.
Legeros, R Z, et al., "In Vitro Formation of Dicalcium Phosphate Dihydrate, CaHPO4.2h2o (DCPD", Scanning Electron Micropscopy, (1983), 407-418.
Legeros, R Z, et al., "The Nature of the Calcified Material Induced by Collagen-Calcium Phosphate Gel in Tooth", Dental Research vol. 57, Special Issue A, Abstract only. Abstract number: 527, (Jan. 1978), 206.
Legeros, Racquel Z, "Biodegradation and Bioresorption of Calcium Phosphate Ceramics", Clinical Materials 14, (1993), 65-88.
Legeros, Raquel Zapanta, "Apatites in Biological Systems", Prog. Crystal Growth Charact. vol. 4, (1981), 1-45.
Lenart, G, et al., "Some Basic Problems in the Examination of the Calcium Hydrogen Phosphates of Bone", Clinical Orthopaedics and Related Research, (1972), 263-272.
Nancollas, G H, et al., "Seeded Growth of Calcium Phosphates: Effect of Different Calcium Phosphate Seed Material", J. Dent. Res. vol. 55, No. 4, (1976), 617-624.
Nevins, Alan, et al., "Hard Tissue Induction Into Pulpless Open-Apex Teeth Using Collagen-Calcium Phosphate Gel", Journal of Endodontics vol. 3, Iss. 11, (1977), 431-433.
Nevins, Alan, et al., "Revitalization of pulpless open apex teeth in rhesus monkeys, using collagen-calcium phosphate gel", J Endod. 2(6), (1976), 159-65.
Roufosse, A. H, "Indentification of Burshite in Newly Deposited Bone Mineral from Embryonic Chicks", Journal of Ultrastructure Research 68, (1979), 235-255.

Tenhuisen, Kevor S, et al., "Formation and properties of a synthetic bone composite: Hydroxyapatite-collagen", Journal of Biomedical Materials Research vol. 29, (1995), 803-810.
Walsh, W R, et al., "Demineralized bone Matrix as a template for mineral-organic composites", Biomaterials 16, (1995), 1363-1371.
U.S. Appl. No. 09/746,921, filed Dec. 22, 2000, Composition and Process for Bone Growth and Repair.
U.S. Appl. No. 11/383,309, filed May 15, 2006, Composition and Process for Bone Growth and Repair.
U.S. Appl. No. 12/849,414, filed Aug. 3, 2010, Composition and Process for Bone Growth and Repair.
U.S. Appl. No. 09/023,617, filed Feb. 13, 1998, Implantable Putty Material.
U.S. Appl. No. 10/739,492, filed Dec. 17, 2003, Implantable Putty Material.
U.S. Appl. No. 12/180,035, filed Jul. 25, 2008, Implantable Putty Material.
U.S. Appl. No. 13/297,005, filed Nov. 15, 2011, Bone Void Fillers.
U.S. Appl. No. 11/614,422, filed Dec. 21, 2006, Bone Growth Particles and Osteoinductive Composition Thereof.
"U.S. Appl. No. 11/614,422, Final Office Action mailed Mar. 24, 2009", 8 pgs.
"U.S. Appl. No. 11/614,422, Non Final Office Action mailed Apr. 16, 2008", 6 pgs.
"U.S. Appl. No. 11/614,422, Non Final Office Action mailed Jun. 29, 2009", 6 pgs.
"U.S. Appl. No. 11/614,422, Non Final Office Action mailed Sep. 11, 2008", 8 pgs.
"U.S. Appl. No. 11/614,422, Notice of Allowance mailed Dec. 30, 2009", 7 pgs.
"U.S. Appl. No. 11/614,422, Response filed Jan. 9, 2009", 9 pgs.
"U.S. Appl. No. 11/614,422, Response filed Feb. 5, 2008 to Restriction Requirement mailed Jan. 23, 2008", 2 pgs.
"U.S. Appl. No. 11/614,422, Response filed May 12, 2008 to Non Final Office Action mailed Apr. 16, 2008", 15 pgs.
"U.S. Appl. No. 11/614,422, Response filed Jun. 18, 2009 to Final Office Action mailed Mar. 24, 2009", 7 pgs.
"U.S. Appl. No. 11/614,422, Response filed Aug. 25, 2009 to Non Final Office Action mailed Jun. 29, 2009", 7 pgs.
"U.S. Appl. No. 11/614,422, Restriction Requirement mailed Jan. 23, 2008", 9 pgs.
"International Application Serial No. PCT/US2007/085853, International Search Report mailed Mar. 7, 2008", 5 pgs.
Alpaslan, C., et al., "Bone reaction to subperiosteally implanted hydroxyapatite/collagen/glycosaminoglycans and coral in the guinea pig", Oral Surg. Oral Med. Oral Path., vol. 77, No. 4 (1994), 335-340, 5 pgs.
Asahina, I., et al., "Repair of Bone Defect in Primate Mandible using a Bone Morphogenetic Protein (BMP)-Hydroxyapatite-Collagen Composite", J. Med. Dent. Sci., vol. 44, (1997), 63-70.
Bar-Shavit, Z., et al., "Glucocorticoids Modulate Macrophage Surface Oligo saccharides and Their Bone Binding Activity", J. Clin. Invest., vol. 73, (1984), 1277-1283.
Benque, E., et al., "Tomodensitometric and Histologic Evaluation of the Combined Use of a Collagen Membrane and a HydroxyapatiteSpacer for Guided Bone Regeneration: A Clinical Report", Int. J. Oral Maxillofac. Implants, vol. 14, (1999), 258-264.
Borsato, K., et al., "Measurement of Partition of Stress Between Mineral and Collagen Phases in Bone Using X-ray Diffraction Techniques", J. Biomechanics, vol. 30, No. 9, (1997), 955-957.
Cornell, C., et al., "Initial clinical experience with use of Colla graft as a bone graft substitute", Techniques Orthop., vol. 7, No. 2, (1992), 55-63.
Cornell, C., et al., "Multicenter Trial of Collagraft as Bone Graft Substitute", J. Orthop. Trauma, vol. 5, No. 1, (1991), 1-8.
Galbavy, S., et al., "AtelocollagenlHydroxylapatite Composite Material as Bone Defects Fillers in the Experiment on Rats", Bratisl. Med. J., vol. 96, (1995), 368-370.
Grigoryan, A., et al., "Time Course of Bone Defect Healing After Implantation in Them of Collagen-Hydroxyapatite Complexes: Experimental and Morphological Study", Stomatologia, vol. 75, (1996), 13-16.

(56) References Cited

OTHER PUBLICATIONS

Hamson, K., et al., "Preliminary Experience with a Novel Model Assessing In Vivo Mechanical Strength of Bone Grafts and Substitute Materials", Calcif. Tissue Int., vol. 57, (1995), 64-68.
Hsu, F., et al., "Microspheres of hydroxyapatite Ire constituted collagen as supports for osteoblast cell growth", Biornaterials, vol. 20, (1999), 1931-1936.
Katthagen, B., et al., "Experimental Animal Investigation of Bone Regeneration with Collagen-Apatite", Arch. Orthop. Trauma Surg. vol. 103, (1984), 291-302.
Kocialkowski, A., et al., "Clinical Experience with a New Artificial Bone Graft: Preliminary Results of a Prospective Study", Injury: The British Journal of Accident Surgery, vol. 21, (1990), 142-144.
Kubler, N., et al., "Bone Morphogenetic Protein-Mediated Interaction of Periosteum and Diaphysis", Clincal Orthopedics and Related Research, vol. 258, (1990), 279-294.
Linder, L., et al., "Electron Microscopic Analysis of the Bone-Titanium Interface", Acta Orthop. Scand., vol. 54, (1983), 45-52.
Lindholm, T., et al., "The role of autogeneic bone marrow in the repair of a skull trephine defect filled with hydroxyapatite granules in the rabbit", Int. J. Oral Maxillofac. Surg., vol. 23, (2004), 306-311.
Mehlisch, D., et al., "Histologic evaluation of the bonelgraft interface after mandibular augmentation with hydroxylapatitelpurified fibrillar collagen composite implants", Oral Surg. Oral Med. Oral Pathol., vol. 70, (1990), 685-692.
Minabe, M., et al., "Histological Study fo the Hydroxyapatite-Collagen Complex Implants in Periodontal Osseous Defects in Dogs", J.Periodontol.,, (Oct. 1988), 671-678.
Mittelmeier, H., et al., "Clinical Experience in the Implantation of Collagen-Apatite for Local Bone Regeneration", Z. Orthop., vol. 121, (1983), 115-123.
Noah, E.M., et al., "Impact of Sterilization of the Porous Design and Cell Behavior in Collagen Sponges Prepared for Tissue Engineering", Biomaterials, vol. 23, (2002), 2855-2861.
Pasquier, G., et al., "Injectable percutaneous bone biomaterials: an experimental study in a rabbit model", J. Mat. Sci. Mat. Med., vol. 7, No. 11, (1996), 683-690.
Pohunkova, H., et al., "Reactivity and the fate of some composite bioimplants based on collagen in connective tissue", Biomaterials, vol. 16, (1995), 67-71.
Rovira, A., et al., "Colonization of a calcium phosphate/elastin-solubilized peptide-collagen composite material by human osteoblasts", Biornaterials, vol. 17, (1996), 1535-1540.
St. John, K., et al., "Response of Canine Boneto a Synthetic Bone Graft Material", Clin. Mat., vol. 12, (1993), 49-55.
Suganuma, J., et al., "In vivo Evaluation of Collagen-Coated Dacron Fiber in Bone", Clin. Mat., vol. 15, (1994), 43-50.
Zerwekh, J., et al., "Fibrillar Collagen-Biphasic Calcium Phosphate Composite as a Bone Graft Substitute for Spinal Fusion", J. Orthop. Res., vol. 10, (1992), 562-572.
"U.S. Appl. No. 09/023,617, Advisory Action mailed Apr. 23, 2002", 3 pgs.
"U.S. Appl. No. 09/023,617, Final Office Action mailed Nov. 23, 2001", 5 pgs.
"U.S. Appl. No. 09/023,617, Non Final Office Action mailed Apr. 24, 2001", 6 pgs.
"U.S. Appl. No. 09/023,617, Notice of Allowance mailed Sep. 15, 2003", 6 pgs.
"U.S. Appl. No. 09/023,617, Response filed Mar. 20, 2002 to Final Office Action mailed Nov. 23, 2001", 6 pgs.
"U.S. Appl. No. 09/023,617, Response filed Jun. 21, 2000 to Restriction Requirement mailed Jun. 15, 2000", 2 pgs.
"U.S. Appl. No. 09/023,617, Response filed Jul. 26, 1999 to Restriction Requirement mailed Jun. 24, 1999", 2 pgs.
"U.S. Appl. No. 09/023,617, Response filed Aug. 24, 2001 to Non Final Office Action mailed Apr. 24, 2001", 6 pgs.
"U.S. Appl. No. 09/023,617, Restriction Requirement mailed Jun. 15, 2000", 6 pgs.
"U.S. Appl. No. 09/023,617, Restriction Requirement mailed Jun. 24, 1999", 5 pgs.
"U.S. Appl. No. 09/746,921, Advisory Action mailed Nov. 8, 2005", 3 pgs.
"U.S. Appl. No. 09/746,921, Examiner Interview Summary mailed Apr. 1, 2002", 1 pg.
"U.S. Appl. No. 09/746,921, Final Office Action mailed Feb. 9, 2007", 14 pgs.
"U.S. Appl. No. 09/746,921, Final Office Action mailed Feb. 25, 2003", 14 pgs.
"U.S. Appl. No. 09/746,921, Final Office Action mailed Jul. 27, 2005", 10 pgs.
"U.S. Appl. No. 09/746,921, Final Office Action mailed Dec. 2, 2004", 12 pgs.
"U.S. Appl. No. 09/746,921, Non Final Office Action mailed Feb. 27, 2006", 7 pgs.
"U.S. Appl. No. 09/746,921, Non Final Office Action mailed Jul. 16, 2002", 13 pgs.
"U.S. Appl. No. 09/746,921, Non Final Office Action mailed Jul. 31, 2006", 10 pgs.
"U.S. Appl. No. 09/746,921, Non Final Office Action mailed Nov. 18, 2003", 15 pgs.
"U.S. Appl. No. 09/746,921, Response filed Feb. 1, 2002 to Restriction Requirement mailed Nov. 1, 2001", 2 pgs.
"U.S. Appl. No. 09/746,921, Response filed May 9, 2006 to Non Final Office Action mailed Feb. 27, 2006", 6 pgs.
"U.S. Appl. No. 09/746,921, Response filed May 11, 2005 to Final Office Action mailed Dec. 2, 2004", 12 pgs.
"U.S. Appl. No. 09/746,921, Response filed May 18, 2004 to Non Final Office Action mailed Nov. 18, 2003", 15 pgs.
"U.S. Appl. No. 09/746,921, Response filed Aug. 25, 2003 to Final Office Action mailed Feb. 25, 2003", 11 pgs.
"U.S. Appl. No. 09/746,921, Response filed Sep. 13, 2004 to Restriction Requirement mailed Aug. 13, 2004", 3 pgs.
"U.S. Appl. No. 09/746,921, Response filed Oct. 17, 2005 to Final Office Action mailed Jul. 27, 2005", 9 pgs.
"U.S. Appl. No. 09/746,921, Response filed Nov. 20, 2006 to Non Final Office Action mailed Jul. 31, 2006", 6 pgs.
"U.S. Appl. No. 09/746,921, Response filed Nov. 25, 2002 to Non Final Office Action mailed Jul. 16, 2002", 9 pgs.
"U.S. Appl. No. 09/746,921, Restriction Requirement mailed Aug. 13, 2004", 6 pgs.
"U.S. Appl. No. 09/746,921, Restriction Requirement mailed Nov. 1, 2001", 5 pgs.
"U.S. Appl. No. 10/739,492, Advisory Action mailed Feb. 5, 2008", 3 pgs.
"U.S. Appl. No. 10/739,492, Final Office Action mailed Oct. 5, 2007", 6 pgs.
"U.S. Appl. No. 10/739,492, Non Final Office Action mailed May 28, 2008", 11 pgs.
"U.S. Appl. No. 10/739,492, Non Final Office Action mailed Oct. 12, 2006", 7 pgs.
"U.S. Appl. No. 10/739,492, Response filed Jan. 10, 2007 to Non Final Office Action mailed Oct. 12, 2006", 4 pgs.
"U.S. Appl. No. 10/739,492, Response filed Jul. 11, 2006 to Restriction Requirement mailed Jul. 3, 2006", 2 pgs.
"U.S. Appl. No. 10/739,492, Response filed Dec. 10, 2007 to Final Office Action mailed Oct. 5, 2007", 7 pgs.
"U.S. Appl. No. 10/739,492, Restriction Requirement mailed Jul. 3, 2006", 7 pgs.
"U.S. Appl. No. 11/383,309, Advisory Action mailed Dec. 15, 2008", 3 pgs.
"U.S. Appl. No. 11/383,309, Appeal Brief filed Sep. 11, 2009", 42 pgs.
"U.S. Appl. No. 11/383,309, Appeal Brief filed Nov. 5, 2009", 14 pgs.
"U.S. Appl. No. 11/383,309, Final Office Action mailed Aug. 18, 2008", 10 pgs.
"U.S. Appl. No. 11/383,309, Non Final Office Action mailed Feb. 3, 2010", 21 pgs.
"U.S. Appl. No. 11/383,309, Non Final Office Action mailed Mar. 31, 2008", 11 pgs.
"U.S. Appl. No. 11/383,309, Non Final Office Action mailed Apr. 13, 2009", 16 pgs.
"U.S. Appl. No. 11/383,309, Response filed Jan. 21, 2009 to Advisory Action mailed Dec. 15, 2008", 14 pgs.

(56) References Cited

OTHER PUBLICATIONS

"U.S. Appl. No. 11/383,309, Response filed Jan. 22, 2008 to Restriction Requirement mailed Jan. 10, 2008", 3 pgs.
"U.S. Appl. No. 11/383,309, Response filed May 6, 2008 to Non Final Office Action mailed Mar. 31, 2008", 12 pgs.
"U.S. Appl. No. 11/383,309, Response filed Nov. 18, 2008 to Final Office Action mailed Aug. 18, 2008", 13 pgs.
"U.S. Appl. No. 11/383,309, Restriction Requirement mailed Jan. 10, 2008", 13 pgs.
"U.S. Appl. No. 12/180,035, Advisory Action mailed Jan. 24, 2012", 4 pgs.
"U.S. Appl. No. 12/180,035, Advisory Action mailed Mar. 12, 2010", 4 pgs.
"U.S. Appl. No. 12/180,035, Examiner Interview Summary mailed Sep. 27, 2011", 2 pgs.
"U.S. Appl. No. 12/180,035, Final Office Action mailed Sep. 27, 2011", 8 pgs.
"U.S. Appl. No. 12/180,035, Final Office Action mailed Nov. 16, 2009", 12 pgs.
"U.S. Appl. No. 12/180,035, Non Final Office Action mailed Dec. 27, 2010", 14 pgs.
"U.S. Appl. No. 12/180,035, Non Final Office Action mailed Apr. 16, 2009", 10 pgs.
"U.S. Appl. No. 12/180,035, Non Final Office Action mailed Jun. 10, 2010", 13 pgs.
"U.S. Appl. No. 12/180,035, Preliminary Amendment mailed Jul. 25, 2008", 5 pgs.
"U.S. Appl. No. 12/180,035, Response filed Jun. 22, 2011 to Non Final Office Action mailed Dec. 27, 2010", 9 pgs.
"U.S. Appl. No. 12/180,035, Response filed Jul. 16, 2009 to Non Final Office Action mailed Apr. 16, 2009", 9 pgs.
"U.S. Appl. No. 12/180,035, Response filed Dec. 22, 2011 to Final Office Action mailed Sep. 27, 2011", 8 pgs.
"U.S. Appl. No. 12/180,035, Response received Feb. 16, 2010 to Final Office Action mailed Nov. 16, 2009", 13 pgs.
"U.S. Appl. No. 12/180,035, Response received Oct. 11, 2010 to Non Final Office Action mailed Jun. 10, 2010", 7 pgs.
"U.S. Appl. No. 12/180,035, Second Preliminary Amendment filed Nov. 24, 2008", 3 pgs.
"U.S. Appl. No. 12/849,414, Non Final Office Action mailed Sep. 23, 2011", 17 pgs.
"U.S. Appl. No. 12/849,414, Preliminary Amendment filed Aug. 3, 2010", 7 pgs.
"Australian Application Serial No. 2007334213, Office Action mailed Jan. 9, 2012", 2 pgs.
"Canadian Application Serial No. 2,280,966, Office Action Oct. 3, 2007", 2 pgs.
"Canadian Application Serial No. 2,280,966, Office Action mailed Apr. 27, 2011", 2 Pgs.
"Canadian Application Serial No. 2,280,966, Office Action mailed Jul. 30, 2006", 2 pgs.
"Canadian Application Serial No. 2,280,966, Office Action mailed Nov. 9, 2009", 3 pgs.
"Canadian Application Serial No. 2,280,966, Office Action Response filed Nov. 9, 2011", 4 pgs.
"Canadian Application Serial No. 2,280,966, Response filed Jan. 29, 2007 to Office Action mailed Jul. 31, 2006", 7 pgs.
"Canadian Application Serial No. 2,280,966, Response filed Mar. 28, 2008 to Office Action mailed Oct. 3, 2007", 12 pgs.
"Canadian Application Serial No. 2,280,966, Response filed May 5, 2010 to Office Action mailed Nov. 9, 2009", 5 pgs.
"Canadian Application Serial No. 2,446,840, Office Action mailed Jul. 27, 2011", 3 pgs.
"Characterization of Osteoinductive Potential", Orthovita Products, http://www.orthovita.com/products/vitoss/osteoinductive.html, (Jan. 2004), 3 pgs.
"Chondrogenesis and Osteogenesis: Growth Factors", Abstract Nos. 917-921, 162a.
"European Application Serial No. 01991379.7, Office Action mailed Jun. 17, 2005", 5 pgs.
"European Application Serial No. 07013717.9, European Search Report mailed Sep. 4, 2007", 8 pgs.
"European Application Serial No. 07013717.9, European Search Report mailed Sep. 10, 2007", 5 pgs.
"European Application Serial No. 07013717.9, Office Action mailed Apr. 1, 2008", 2 pgs.
"European Application Serial No. 07864863.1, Office Action mailed Feb. 22, 2011", 5 pgs.
"European Application Serial No. 07864863.1, Office Action mailed Nov. 6, 2009", 5 pgs.
"European Application Serial No. 07864863.1, Response filed Mar. 16, 2010 to Office Action mailed Nov. 6, 2009", 10 pgs.
"European Application Serial No. 07864863.1, Response filed Nov. 4, 2011 to Office Action mailed Feb. 22, 2011", 7 pgs.
"European Application Serial No. 98908535.2, Office Action mailed Feb. 1, 2006", 4 pgs.
"European Application Serial No. 98908535.2, Office Action mailed Feb. 2, 2005", 4 pgs.
"European Application Serial No. 98908535.2, Office Action mailed Nov. 6, 2006", 3 pgs.
"European Application Serial No. 98908535.2, Response filed May 29, 2006 to Office Action mailed Feb. 1, 2006", 9 pgs.
"European Application Serial No. 98908535.2, Response filed Aug. 2, 2005 to Office Action mailed Feb. 2, 2005", 8 pgs.
"European Application Serial No. 98908535.2, Search Report mailed Mar. 25, 2004", 3 pgs.
"Fundamental of Bone Physiology", Therics, 4 pgs.
"International Application Serial No. PCT/US01/49314, International Search Report mailed Apr. 7, 2002", 5 pgs.
"International Application Serial No. PCT/US01/49314, International Search Report mailed Apr. 7, 2002", 4 pgs.
"International Application Serial No. PCT/US2001/049314, International Preliminary Examination Report mailed Oct. 24, 2002", 2 pgs.
"International Application Serial No. PCT/US2007/085853, International Preliminary Report on Patentability mailed Jun. 23, 2009", 8 pgs.
"International Application Serial No. PCT/US2007/085853, International Search Report mailed Jul. 3, 2008", 4 pgs.
"International Application Serial No. PCT/US2011/060823, International Search Report Jan. 24, 2012", 3 pgs.
"International Application Serial No. PCT/US2011/060823, Written Opinion Jan. 24, 2012", 4 pgs.
"Japanese Application Serial No. 1998535914, Office Action mailed Sep. 30, 2008", 3 pgs.
"Japanese Application Serial No. 1998535914, Response filed Aug. 10, 2009", w/Translation, 40 pgs.
"Japanese Application Serial No. 2002-552590, Office Action mailed Mar. 31, 2009", 4 pgs.
"Japanese Application Serial No. 2002-552590, Office Action mailed Aug. 19, 2008", 6 pgs.
"Japanese Application Serial No. 2002-552590, Office Action mailed Dec. 20, 2011", 2 pgs.
"Japanese Application Serial No. 2002-552590, Office Action Received May 6, 2011", 10 pgs.
Oxlund, H., et al., "The roles of hyaluronic acid, collagen and elastin in the mechanical properties of connective tissues", J Anat., 131(Pt 4), (Dec. 1980), 611-20.
"U.S. Appl. No. 12/180,035, Response filed Feb. 28, 2013 to Non Final Office Action mailed Nov. 28, 2012", 6 pgs.
"Canadian Application Serial No. 2,673,337, Response filed Feb. 7, 2013 to Office Action mailed Aug. 9, 2012", 7 pgs.
Landesman, Richard, et al., "In Vivo Analysis of the Half-Life of the Osteoinductive Potential of Demineralized Bone Matrix Using Diffusion Chambers", Calcif Tissue Int. vol. 45, (1989), 348-353.
Pappalardo, S, et al., "How to biomaterials affect the biological activities and responses of cells? An in-vitro study", Minerva Stomatol vol. 59, (2010), 445-464.
Urist, Marshall R, et al., "Preservation and Biodegration of the Morphogenetic Property of Bone Matrix", J. theor. Biol. vol. 38, (1973), 155-167.
"U.S. Appl. No. 12/180,035, Examiner Interview Summary mailed Mar. 14, 2012", 3 pgs.

(56) References Cited

OTHER PUBLICATIONS

"U.S. Appl. No. 12/180,035, Response filed Mar. 20, 2012 to Final Office Action mailed Sep. 27, 2011", 9 pgs.

"U.S. Appl. No. 12/849,414 , Response filed Mar. 23, 2012 to Non Final Office Action mailed Sep. 23, 2011", 8 pgs.

"Australian Application Serial No. 2007334213, Response filed Apr. 19, 2012 to First Examiners Report mailed Jan. 9, 2012", 9 pgs.

"Japanese Application Serial No. 1998535914, Office Action Mailed Jan. 24, 2012", W/ English Translation, 24 Pgs.

Cheung, D. T, et al., "The effect of gamma-irradiation on collagen molecules, isolated alpha-chains, and crosslinked native fibers.", J Biomed Mater Res., 24(5), (May 1990), 581-9.

Chu, C. C, et al., "The effect of gamma irradiation on the enzymatic degradation of polyglycolic acid absorbable sutures", J Biomed Mater Res., 17(6), (Nov. 1983), 1029-40.

Hallfeldt, K. K, et al., "Sterilization of partially demineralized bone matrix: the effects of different sterilization techniques on osteogenetic properties", J Surg Res., 59(5), (Nov. 1995), 614-20.

Hamada, K., et al., "Hydrothermal modification of titanium surface in calcium solutions", Biomaterials, 23, (2002), 2265-2272.

Ho, Hsiu-O, et al., "Characterization of collagen isolation and application of collagen gel as a drug carrier", Journal of Controlled Release, 44, (1997), 103-112.

Ijiri, S., et al., "Effect of sterilization on bone morphogenetic protein", J Orthop Res., 12(5), (Sep. 1994), 628-36.

Katz, R. W, et al., "Radiation-sterilized insoluble collagenous bone matrix is a functional carrier of osteogenin for bone induction", Calcif Tissue Int., 47(3), (Sep. 1990), 183-5.

Kim, H. M, et al., "Effect of heat treatment on apatite-forming ability of Ti metal induced by alkali treatment", J Mater Sci Mater Med., 8(6), (Jun. 1997), 341-7.

Lee, K. Y, et al., "Preparation of Caclium Phosphate Paste Composites with Demineralized Bone Matrix", Key Engineering Materials, (vols. 330-332), (2007), 803-806.

Legeros, Racquel Zapanta, "Calcium Phosphate-Based Osteoinductive Materials", Chem. Rev., 108, (2008), 4742-4753.

Liu, B., et al., "The effect of gamma irradiation on injectable human amnion collagen", J Biomed Mater Res., 23(8), (Aug. 1989), 833-44.

Munting, E., et al., "Effect of sterilization on osteoinduction. Comparison of five methods in demineralized rat bone", Acta Orthop Scand., 59(1), (Feb. 1988), 34-8.

Puolakkainen, "The effect of sterilization on transforming growth factor beta isolated from demineralized human bone", Transfusion, 33(8), (Aug. 1993), 679-85.

Raptopoulou-Gigi, M., et al., "Antimicrobial proteins in sterilised human milk", Br Med J., 1(6052), (Jan. 1, 1977), 12-4.

Reid, B. D, et al., "Gamma processing technology: an alternative technology for terminal sterilization of parenterals", PDA J Pharm Sci Technol., 49(2), (Mar.-Apr. 1995), 83-9.

Schwarz, N., et al., "Irradiation-sterilization of rat bone matrix gelatin", Acta Orthop Scand., 59(2), (Apr. 1988), 165-7.

Soboleva, N. N, et al., "Radiation resistivity of frozen insulin solutions and suspensions", Int J Appl Radiat Isot., 32(10), (Oct. 1981), 753-6.

Su, D., et al., "Sterilization of collagen matrix containing protein growth factors using gamma and electron beam irradiation", Pharmaceutical Research, 12(9), Abstract BIOTEC 2035, (1995), S-87.

Tezcaner, A., et al., "Fundamentals of tissue engineering: Tissues and applications", Technology and Health Care, 10, (2002), 203-216.

Tofighi, A., "Calcium Phosphate Cement (CPC): A Critical Development Path", Key Engineering Materials, (vols. 361-363), (2008), 303-306.

Wientroub, S., et al., "Influence of irradiation on the osteoinductive potential of demineralized bone matrix", Calcif Tissue Int., 42(4), (Apr. 1988), 255-60.

"U.S. Appl. No. 12/180,035, Notice of Allowance mailed Mar. 25, 2013", 6 pgs.

"Collagraft bone Graft Matrix (Contraindications)", Distributed by Zimmer, Inc., Warsaw, Indiana, (Sep. 1992), 1 pg.

"Collagraft Bone Graft Matrix (Indications)", Distributed by Zimmer, Inc., Warsaw, Indiana, (Sep. 1992), 1 pg.

"Collagraft Bone Graft Matrix (Nonosteoinductive Bone Void Filler)", Distributed by Zimmer, Inc., Warsaw, Indiana, (Sep. 1992), 1 pg.

"Collagraft Bone Graft Matriz Strip", Distributed by Zimmer, Inc., Warsaw, Indiana, (Feb. 1994), 6 pgs.

"Collagraft Bone Graft Substitute (Physician Package Insert)", Distribute by Zimmer, Inc., Warsaw, Indiana, (Mar. 1989), 1 pg.

"OP-1: the First Name in BMPs", Stryker Biotech, http://www.opl.com/home.cfm?countryID=5, (Jan. 2004), 3 pgs.

"Osteoinductive", Scientific.net, [Online]. Retrieved from the Internet: <URL: http://www.scientific.net/Osteoinductive.htm>, (Jan. 2004), 1 pg.

"Spinal Technologies:INFUSE Bone Graft/LT-CAGE Lumbar Tapered Fusion Device", Medtronic Sofamor Danek, http://www.medtronicsofamordanek.com/patient-spinal-infuse.html, (Jan. 23, 2004), 4 pgs.

"The Organization of Skeletal Tissues", The Architecture and Cellular Elements of Bone, (Oct. 2000), 4 pgs.

Bentz, Hanne, et al., "Purification and Characterization of a Unique Osteoinductive Factor from Bovine Bone", The Journal of Biological Chemistry, vol. 264, No. 32, (Dec. 1989), 20805-20810.

Bentz, Hanne, et al., "Transforming Growth Factor-β2 Enhances the Osteo-inductive Activity of a Bovine Bone-Derived Fraction Containing Bone Morphogenetic Protein-2 and 3", Matrix, vol. 11, (1991), 269-279.

Block, et al., "Glycol Methacrylate Embedding Technique Emphasizing Cost Containment, Ultrarapid Processing, and Adaptability to a Variety of Staining Techniques", Laboratory medicine 13(5), (May 1982), 290-298.

Boden, Scott D, et al., "Evaluation of a Bovine-Derived Osteoinductive Bone Protein in a Nonhuman Primate Model of Lumbar Spinal Fusion", American Academy of Orthopaedic Surgeons 1996 Annual Meeting—Scientific Program, http://www.aaos.org/wordhtml/anmeet96/sciprog/073.htm, (Feb. 1996), 2 pgs.

Brown, W. E., et al., "Chemical Properties of Bone Mineral", Ann. Res. Mater. Sci., 6, (1976), 213-236.

Brown, W. E., et al., "Crystal Chemistry of Octacalcium Phosphate", Prog. Crystal Growth Charact., 4, (1981), 59-87.

Burwell, R. G, "The function of bone marrow in the incorporation of a bone graft.", Clin Orthop Relat Res., 200, (Nov. 1985), 125-141.

Cheng, Hongwei, et al., "Osteogenic Activity of the Fourteen Types of Human Bone Morphogenetic Proteins (BMPs)", The Journal of Bone & Joint Surgery 85-A (8), (Aug. 2003), 1544-1552.

Damien, Christopher J, et al., "Bone Graft and Bone Graft Substitutes: A Review of Current Technology and Applications", Journal of Applied Biomaterials, vol. 2, (1991), 187-208.

Delustro, Frank, et al., "Immune Responses to Allogeneic and Xenogeneic Implants of Collagen and Collagen Derivatives", Clinical Orthopaedics and Related Research 260, (Nov. 1990), 263-279.

Derutier, et al., "Biphosphonates: Calcium Antiresorptive Agents", Endocrine Module, [Online]. Retrieved from the Internet: <URL: http://www.auburn.edu/~deruija/endo_bisphos.pdf>, (2002), 1-7.

Endres, M., et al., "Osteogenic Induction of Human Bone Marrow-Derived Mesenchymal Progenitor Cells in Novel Synthetic Polymer-Hydrogel Matrices", Tissue Engineering, vol. 9, No. 4, (2003), 689-702.

Francis, Marion D., et al., "Hydroxyapatite Formation from a Hydrated Calcium Monohydrogen Phosphate Precursor", Calcif. Tissue Res., 6, (1971), 335-342.

Guillemin, et al., "The use of coral as a bone graft substitute", J. Biomed. Mat. Res. 21, (1987), 557-567.

Ho, Hsiu-O, et al., "Characterization of collage isolation and application of collagen gel as a drug carrier", Journal of controlled release, vol. 44, (1997), 103-111.

Hott, et al., "Ceramics in Substitutive and Reconstructive Surgery", P. Vincenzini, ed.,, (1991), 345-352.

Ito, M., et al., "In vitro properties of a chitosan-bondedhydroxyapatite bone filling paste", Biomaterials, vol. 12, (41-45), 1991.

(56) References Cited

OTHER PUBLICATIONS

Itoh, Takashi, et al., "Structural Analysis of Collagen Fibrils in Rat Skin Based on Small-Angle X-Ray-Diffraction Pattern", Jpn. J. Appl. Phys., Part 1, No. 12A, (1996), 6172-6179.

Johnsson, Mats, et al., "The Role of Brushite and Octacalcium Phosphate in Apatite Formation", Critical Reviews in Oral Biology and Medicine, vol. 3, (1993), 61-82.

Kocialkowski, et al., "Bone Grafts, Derivatives & Substitutes", Collagraft Combined with Autogeneic Bone Marrow: Experimental and Clinical Results, Chapter 14, (1994), 271-290.

Lane, et al., "The Use of Composite Bone Graft Materials in a Segmental Femoral Defect Model in the Rat", J. Orthop. Trauma 2(1) (abstract), (1988), 57-58.

Liu, Y. M, et al., "2714 Osteoinductive Implants: the mis-en-scene for drug-bearing biomimetic coatings", Osteoinductive Implants, http://iadr.confex.com/iadr/2004Hawaii/techprogram/abstract_40044.htm, (Jan. 2004), 1 pg.

McIntyre, et al., "Characterization of a Bioceramic Composite for Repair of Large Bone Defects", Ceramic Bulletin 70 (9), (1991), 1499-1503.

Muschler, George F, et al., "Evaluation of Bone-Grafting Materials in a New Canine Segmental Spinal Fusion Model", Journal of Orthopaedic Research, vol. 11, No. 4, (Jul. 1993), 514-524.

Nathan, et al., "Osteogenesis in Rats With an Inductive Bovine Composite", Journal of Orthopaedic Research 6, (1993), 325-334.

Nathan, Ranga M, et al., "Osteogenesis in Rats with an Inductive Bovine Composite", Journal of Orthopaedic Research, vol. 6, No. 3, (1988), 324-334.

Ohura, Kouichiro, et al., "Healing of Segmental Bone Defects in Rats Induced by a Beta-TCP-MCPM Cement Combined with rhBMP-2", Journal of Biomedical Materials Research 44(2), (1999), 168-175.

Peng, Y, et al., "Transcriptional Characterization of Bone Morphogenetic Proteins (BMPs) Mediated Osteogenic Signaling", J. Cell Biochem. vol. 90, No. 6, http://www.ncbi.nlm.nih.gov/entrez/query.fcgi?cmd=Retrieve&db=PubMed&list_uids=14, (Dec. 2003), 1149-1165.

Ronziere, et al., "Analysis of types I, II, III, IX and XI collagens synthesized by fetal bovine chondrocytes in high-density culture", Osteoarthritis and Cartilage 5, (1997), 205-214.

Rosenblatt, et al., "Injectable Collagen as a pH-sensitive hydrogel", Biomaterials, vol. 15, No. 12, (1994), 985-995.

Sampath, et al., "Isolation of Osteogenin, an extracellular matrix-associated, bone-inductive protein, by heparin affinity chromatography", Proc. Natl. Acad. Sci USA 84, (Oct. 1987), 7109-7113.

Stone, et al., "Porcine and Bovine Cartilage Transplants in Cynomolgus Monkey", Transplantation, vol. 63, No. 5, Williams & Wilkins, USA, (Mar. 15, 1997), 640-645.

Takagi, Katsumasa, et al., "The Role of Bone Marrow in Bone Morphogenetic Protein-induced Repair of Femoral Massive Diaphyseal Defects", Clinical Orthopaedics and Related Research, vol. 171, (Dec. 1982), 224-231.

Thorne, et al., "CopiOs Injectible Paste Development Preliminary Disclosure Summary", (2004).

Truumees, et al., "Alternatives to Autologous Bone Harvest in Spine Surgery", The University of Pennsylvania Orthopaedic Journal 12, USA, (1999), 77-88.

Zardiackas, Lyle D, et al., "Torsional Properties of Healed Canine Diaphyseal Defects with a Fibrillar Collegen and Hydroxyapatite/Tricalcium Phosphate Composite", Journal of Applied Biomaterials 5, (1994), 277-283.

"U.S. Appl. No. 12/849,414, Non Final Office Action mailed Jun. 11, 2013", 28 pgs.

"U.S. Appl. No. 12/849,414, Response filed Aug. 9, 2013 to Non Final Office Action mailed Jun. 11, 2013", 9 pgs.

"U.S. Appl. No. 13/297,005, Examiner Interview Summary mailed May 22, 2013", 3 pgs.

"U.S. Appl. No. 13/297,005, Notice of Allowance mailed Aug. 7, 2013", 12 pgs.

"U.S. Appl. No. 13/297,005, Response filed Jun. 24, 2013 to Final Office Action Mar. 22, 2013", 13 pgs.

"Australian Application Serial No. 2012204139, First Examiner Report mailed Apr. 10, 2013", 3 pgs.

"Australian Application Serial No. 2012204139, Response filed Aug. 22, 2013 to First Examination Report mailed Apr. 10, 2013", 11 pgs.

"Canadian Application Serial No. 2,446,840, Office Action mailed Apr. 30, 2013", 4 pgs.

"Canadian Application Serial No. 2,673,337, Office Action mailed Mar. 26, 2013", 2 pgs.

"Canadian Application Serial No. 2,673,337, Response filed Sep. 16, 2013 to Office Action mailed Mar. 26, 2013", 6 pgs.

"European Application Serial No. 07864863.1, Examination Notification Art. 94(3) mailed Mar. 5, 2013", 4 pgs.

"International Application Serial No. PCT/US2011/060823, International Preliminary Report on Patentability mailed May 30, 2013", 6 pgs.

Weadock, K., et al., "Evaluation of collagen crosslinking techniques", Biomater Med Devices Artif Organs., 11(4), (1983-1984), 293-318.

* cited by examiner

BONE GROWTH PARTICLES AND OSTEOINDUCTIVE COMPOSITION THEREOF

This application is a continuation of U.S. application Ser. No. 11/614,422, now issued as U.S. Pat. No. 7,718,616, filed Dec. 21, 2006.

FIELD OF THE INVENTION

The invention relates generally to a composition comprising bone growth particles, a method of making the composition, and a use of the composition in promoting bone growth.

BACKGROUND

The use of osteoinductive proteins or growth factors, such as bone morphogenetic proteins (BMPs), mitogenic growth factors, etc., improves clinical outcomes after surgical reconstruction of skeletal defects (e.g., implants). Such osteoinductive factors induce bone formation by targeting and activating undifferentiated perivascular connective tissue cells. Mitogenic growth factors target and accelerate the osteogenic activity of previously differentiated cells. Although advances have improved the biological activity of osteoinductive factors, their clinical application has been limited by the requirement for a superior tissue scaffold/delivery vehicle.

Autologous bone grafts are the gold standard for restoring skeletal defects because they provide both a natural tissue scaffold and osteoinductive growth factors. Allogenic grafts may also be used, such as demineralized bone matrices. For example, demineralized bone material can be prepared by grinding a bone, demineralizing it with an acid solution, washing with a phosphate buffered solution, washing with ethanol and drying it. Demineralized bone material can also be obtained from a commercial bone or tissue bank (e.g., AlloSource, Denver Colo.). Because autogenic and allogenic sources of human bone are limited and may be expensive or painful to obtain, the use of substitute materials is preferred. Numerous synthetic or modified natural materials have been experimentally evaluated as alternative delivery vehicles, and include but are not limited to products containing hydroxyapatites, tricalcium phosphates, aliphatic polyesters (poly(lactic) acids (PLA), poly(glycolic)acids (PGA), polycaprolactone (PCL), cancellous bone allografts, human fibrin, plaster of Paris, apatite, wollastonite (calcium silicate), glass, ceramics, titanium, devitalized bone matrix, non-collagenous proteins, collagen and autolyzed antigen extracted allogenic bone. However, these synthetic or modified natural materials have yet to result in delivery vehicles having osteoinductivity comparable to autograft or allograft bone sources, or having the capability to enhance the osteoinductivity of these or other osteoinductive materials.

Alternate products are desirable.

SUMMARY OF THE INVENTION

Biocompatible compositions that comprise bone growth particles, a method of making the compositions, and uses of the compositions in promoting bone growth are disclosed. One embodiment is a bone growth-promoting composition comprising collagen and calcium phosphate that can be formulated as a paste or putty. The compositions and methods facilitate skeletal regeneration and provide a scaffold for new bone growth.

The compositions may be formulated as pastes or putties. This provides ease of use and economy of product manufacture. Pastes and putties are soft masses with physical consistencies between a liquid and a solid. Pastes and putties are desirable for surgical bone repair as they can be more easily delivered to difficult surgical sites and molded in site into desired shapes. These products are desirable for the reconstruction of skeletal defects, e.g., in spine, dental, and/or other orthopedic surgeries. They may be used as a substitute for autologous bone grafts or may be used in conjunction with autologous bone grafts.

In one embodiment, engineered (i.e., synthetic) composite products that enhance the in vivo formation of bone tissue and preserves the availability, and thus the functional activity of osteoinductive growth factors are disclosed. Local pH control enhances clinical efficacy of osteogenic proteins, and supplements local availability of essential bone components such as collagen, calcium, and phosphate. Moderately acidic microenvironments likely improve protein-stimulated osteoinduction by enhancing the rates of protein solubilization and protein release from collagen. Supplementing the local concentration of soluble $[Ca^{2+}]$ and $[PO_4^{3-}]$ ions enhances the quantity of bone produced, and increases rate of bone formation by reducing dependence on essential ion diffusion from serum and other body fluids. The resultant increase in local concentration and cellular availability of bone morphogenetic proteins result in improved acidic collagen delivery vehicles.

One embodiment is a biocompatible synthetic bone growth composition comprising a particulate composite of a fibrillar collagen component and a calcium phosphate component. The collagen component may be insoluble collagen (e.g., crosslinked collagen or porous particles). The calcium phosphate component may be acidic calcium phosphate, such as monocalcium phosphate $[Ca(H_2PO_4)_2]$, calcium hydrogen phosphate dihydrate $[CaHPO_4 2H_2O]$, anhydrous calcium hydrogen phosphate $[CaHPO_4]$, partially dehydrated calcium hydrogen phosphate $[CaHPO_4 xH_2O$, where x is between and includes 0 and 2] and/or calcium pyrophosphate $[2CaO.P_2O_5]$. In one embodiment, the composition contains an osteoinductive component, e.g., a purified bone growth factor, a recombinant bone growth factor, a bone marrow component, a blood component, demineralized bone, autologous bone, bone marrow aspirate, etc. In one embodiment, the composition pH ranges from about pH 5 to about pH 7.

Another embodiment is a process for producing a bone growth composition. A collagen component is combined with a calcium phosphate component to produce a mineralized collagen component. The mineralized collagen component may be prepared as a collagen gel, which may be frozen and lyophilized into a product referred to as a sponge. Particles of the mineralized collagen component (e.g. sponge) may be prepared by grinding, milling, chopping and/or molding the mineralized collagen component. The particulate composition may be packaged as a kit that may include a device (e.g., container) for mixing the particles with a fluid. An osteoinductive component may be added, either before or after forming the particles.

Another embodiment is a method of facilitating bone growth in a patient by adding an osteoinductive component to a particulate mineralized collagen component and implanting the composition in the patient. The composition may be injected into and/or molded to fit a surgical site.

These and other embodiments will be further appreciated with respect to the following drawings, description, and examples.

DETAILED DESCRIPTION

Figures 1, 2:
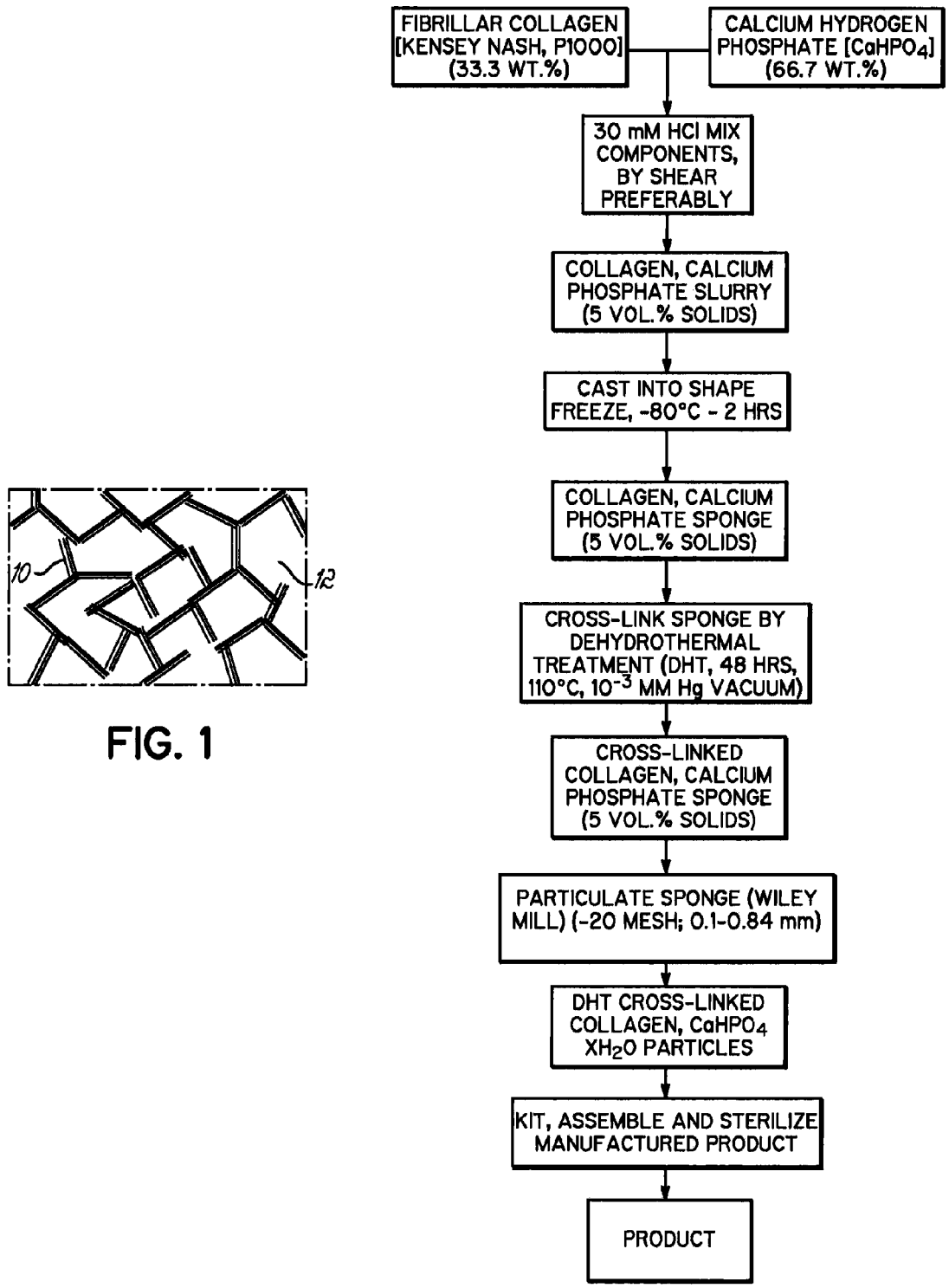
FIG. 1 shows a schematic representation of a collagen scaffold.
FIG. 2 shows a flow chart representing a process for making a mineralized collagen component.

The basic elements required for bone formation include a three-dimensional, open-porosity tissue scaffold, cells, and osteoinductive signaling molecules to stimulate cell differentiation, proliferation and matrix formation. Successful bone formation requires that these elements be combined in a well-coordinated spatial and time dependent fashion. The relative contribution of each element may vary, e.g., according to differences in patient age, gender, health, systemic conditions, habits, anatomical location, etc.

Embodiments for improved bone formation and healing include the following: biocompatible, open-porous bone tissues scaffold, enhanced local concentration of soluble bone mineral elements such as calcium and phosphate, and preserved osteoinductive protein solubility. Each is subsequently analyzed.

A biocompatible, open-porous bone tissue scaffold restores function and/or regenerates bone by providing a temporary matrix for cell proliferation and extracellular matrix deposition with consequent bone in-growth until new bony tissue is restored and/or regenerated. The matrix may also provide a template for vascularization of this tissue. The scaffold may actively participate in the regenerative process through the release of growth differentiation factors.

The macro and micro-structural properties of the scaffold influence the survival, signaling, growth, propagation, and reorganization of cells. They may also influence cellular gene expression and phenotype preservation. The following properties contribute to scaffold characteristics for bone formation: cell biocompatiability, surface chemistry, biodegradability, porosity, and pore size.

In one embodiment, the composition comprises fibrillar collagen. Collagen is the main protein of connective tissue in animals and the most abundant protein in mammals. Bone is composed of strong, fibrillar bundles of collagen encased within a hard matrix of a calcium phosphate known as hydroxylapatite. Collagen is also a constituent in cartilage, tendon and other connective tissues.

The collagen protein possesses a distinctive triple-helix tertiary structure of three polypeptide chains supercoiled about a common axis and linked by hydrogen bonds. At least nineteen distinct molecules have been classified as collagens, and specific types are associated with particular tissues. Collagen can be converted into gelatin by boiling or treating with an acid. The solubility of collagen is affected by its conformation and extent of associations, whereby newly synthesized collagen chains are generally soluble but after formation of fibrils, they become essentially insoluble.

Collagen fibrils, referred to as fibrillar collagen, result from covalent cross-linking between the supercoiled chains by an enzymatic mechanism that strengthens and stabilizes the chains. Fibrillar collagen may be obtained from native sources such as human or animal dermis, tendon, cartilage or bone. It is generally recovered by proteolytically degrading natural collagen crosslinks to produce tropocollagen. Tropocollagen, the basic amino acid component, is soluble with acidic solutions (in one embodiment, between pH 3 to pH 4). These solutions can be cleaned and purified prior to collagen fiber reassembly by pH neutralization. Fibrillar collagen is generally less dense, less soluble, and swells more in solution than non-fibrillar collagen.

Due to its high degree of biocompatibility with the human body, collagen has been successfully used in a variety of medical and dental applications for many years with minimal adverse responses. During its manufacture, potentially antigenic portions of the collagen molecule are removed, resulting in a product that is highly biocompatible and well-tolerated by the tissue. Collagen is also chemotactic for fibroblasts and other cells involved in bone tissue repair. Collagen biocompatibility ensures that the products are well integrated in the host tissue without eliciting an immune response.

Collagen used in the particulate composition may be from any source. These include natural sources such as human and mammalian tissues, and synthetic sources manufactured using recombinant technologies. It may be of any type (e.g., collagen Types I, II, III, X and/or gelatin). In one embodiment, collagen used is Type I collagen. In one embodiment, collagen is derived from bovine dermis. In one embodiment, fibrillar collagen is derived from bovine dermis manufactured by Kensey Nash Corporation (Exton Pa.) under the name Semed F. In one embodiment, fibrillar collagen may be obtained from Kensey Nash Corporation under the name P1000. In one embodiment, the particles comprise at least about 33 percent by dry weight collagen. In another embodiment, the particles comprise from about 25 percent to about 75 percent dry weight collagen.

The surface chemistry of the scaffold can control and affect cellular adhesion. It can also influence the solubility and availability of proteins essential for intracellular signaling. Intracellular signaling maximizes osteoinductivity through controlled cellular differentiation, proliferation, and stimulation.

Collagen fabricates the disclosed structural scaffold and provides a physical and chemical milieu favorable to bone regeneration. Collagen also provides a favorable extracellular matrix for bone forming cells, e.g., osteoblasts, osteoclasts, osteocytes, etc. The bone forming cells' natural affinity for the collagen matrix has been demonstrated to favorably influence the function and signaling required for normal cellular activity.

The degradation rate of the scaffold should ideally match the bone-healing rate. Slower degradation rates can hinder the rate of remodeled, load-bearing bone formation. Faster degradation can result in unhealed defects.

The solubility and resorption of collagen is affected by its conformation and the degree of collagen cross-linking. The in vivo solubility and resorption of collagen is also influenced by the local concentration of proteolytic agents and vascularity at the site.

In one embodiment, the composition is crosslinked to control the solubility and the extent and rate of collagen resorption. Collagen crosslinking may occur by various methods such as dehydrothermal (DHT), UV light exposure, chemical crosslinking with aldehydes (i.e. glyceraldehyde, formaldehyde, glutaraldehyde), carbodiimides and various amino acids. The crosslinking conditions will preserve the in vivo lifetime of the composition for up to about twelve weeks, allowing it to function as a scaffold for bone healing. Collagen is eventually absorbed into the surrounding tissue by host enzymes. In one embodiment, uncrosslinked collagen may be a component of the composition.

Scaffolds desirably posses an open pore, fully interconnected geometry to allow homogeneous and rapid cell ingrowth, and facilitate vascularization of the construct from the surrounding tissue.

To this end, the total pore volume porosity of the scaffold simulates that of cancellous bone. Cancellous bone is a highly porous structure (about 50 vol. % to about 90 vol. %) arranged in a sponge-like form, with a honeycomb of branching bars, plates, and rods of various sizes called trabeculae. The synthetic scaffold must ensure pore interconnectivity to allow for the diffusion of nutrients and gases and for the removal of metabolic waste resulting from the activity of the cells within the scaffold. It is generally accepted by one skilled in the art that the pore diameters should be within the range of about 200 μm to about 900 μm range for ideal bone formation. Smaller pores can occlude and restrict cellular penetration, matrix production, and tissue vascularization. Larger pores can detrimentally influence the mechanical properties of the structural scaffold.

The disclosed method produces a synthetic scaffold that mimics the natural structural design of bone for bone formation. In one embodiment, the scaffold is fabricated using fibrillar collagen. Fibrillar collagen is the cytoskeletal filament within the matrix of all tissues and organs. In addition to being a fundamental element of natural bone, fibrillar collagen allows the formation of a scaffold with high surface area and an interconnected network of high porosity, as shown in FIG. 1. The total pore volume is made up of both micropores 10, which is the space between collagen strands within the fibril, and macropores 12, which is the space between collagen fibrils. In one embodiment, the composition matches the porosity of cancellous bone, with total pore volumes ranging between about 50 vol. % to about 97 vol. % and pore diameters ranging between 1 μm and 1000 μm.

Enhancing local concentration of soluble bone mineral elements, such as $[Ca^{2+}]$ and/or $[PO_4^{3-}]$, contributes to improved bone formation and healing.

Calcium phosphate based products have been used for bone repair for over 80 years. Their many desirable properties include similarity in composition to bone mineral, bioactivity (ability to form apatitic or carbonated hydroxylapatite on their surfaces), ability to promote cellular function and expression, ability to form a direct strong interface with bone, and osteoconductivity (ability to provide a scaffold or template for the formation of new bone). Commercially available calcium phosphate biomaterials differ in origin (e.g., natural or synthetic), composition (e.g., hydroxylapatite, beta-tricalcium phosphate, and biphasic calcium phosphate), physical forms (e.g., particulates, blocks, cements, coatings on metal implants, composites with polymers), and physicochemical properties. Subtle differences in chemical composition and crystalline structure may significantly impact their in vivo physical and biological performance.

The disclosed composition and method supplements the local availability of essential soluble bone components, e.g., calcium and phosphate. Biologically compatible, sparingly soluble calcium phosphates are suitable supplements to locally increase the supply of soluble calcium $[Ca^{2+}]$ and phosphate $[PO_4^{3-}]$ ions. As shown in Table 1 calcium phosphate salts solubilize at different equilibrium ionic concentrations, where the local supplemented concentrations of calcium $[Ca^{2+}]$ and phosphate $[PO_4^{3-}]$ ions can vary by more than four orders of magnitude. Calcium hydrogen phosphate (dical), an example of a calcium phosphate additive used in the disclosed composition, provides about 200 to about 300 times the concentration of soluble mineral elements in comparison to conventional calcium phosphates, such as tricalcium phosphate (TCP) $(Ca_3(PO_4)_2)$ or tetracalcium phosphate (TTCP) $(Ca_4(PO_4)_2(OH)_2)$ or calcium hydroxyapatite (HA) $(Ca_5(PO_4)_3(OH))$.

TABLE 1

Equilibrium solubility of calcium and phosphate ions from several different biologically compatible calcium phosphate salts.

| | Equilibrium $[Ca^{2+}]$ | Equilibrium $[PO_4^{3-}]$ | Insoluble fraction [200 mg/cc] |
|---|---|---|---|
| Plasma | 2,200.0 μM | 1,100.0 μM | — |
| $Ca(H_2PO_4)_2$ (Monocal) | 14,300.0 μM | 28,600.0 μM | 97.0000 wt. % |
| $CaHPO_4$ (Dical) | 480.0 μM | 480.0 μM | 99.9700 wt. % |
| $Ca_3(PO_4)_2$ (TCP) | 1.4 μM | 0.9 μM | 99.9999 wt. % |
| $Ca_5(PO_4)_3(OH)$ (HA) | 2.2 μM | 1.3 μM | 99.9999 wt. % |
| $Ca_4(PO_4)_2(OH)_2$ (TTCP) | 28.2 μM | 14.1 μM | 99.9994 wt. % |

Dical is soluble and does not require osteoclastic resorption for biodegradation. It resorbs slowly enough that products can be designed to supplement the soluble mineral ion concentration for several weeks.

Local supplementation of soluble $[Ca^{2+}]$ and $[PO_4^{3-}]$ ions enhanced the quantity of bone produced and increased its rate of formation in animals. Without being bound by a specific theory, it is believed that the use of a soluble form a calcium phosphate reduces the healing rate dependence on local osteoclastic resorption and essential ion diffusion from plasma fluids.

The method and composition preserved osteoinductive protein solubility. Osteoinduction is the process by which stem cells and osteoprogenitor cells are recruited to a bone-healing site and are stimulated to undergo the osteogenic differentiation pathway. Classic synthetic, biodegradable scaffolds are only osteoconductive and require combination with an inductive bone-forming agent to stimulate and accelerate bone healing.

Bone growth factor cytokines, also known as bone morphogenetic proteins (BMPs), are entrapped at high concentration within bone and are secreted by many bone-forming cell types. The primary function of BMPs is cellular signaling. Intracellular signaling occurs through the binding of a soluble growth factor to a specific cell receptor site. This signal pathway stimulates several different and important bone healing events, including the proliferation, migration, and differentiation of bone forming cells. The cells are, in turn, responsible for the synthesis of other proteins and growth factors that are important for regulating and controlling bone tissue formation. Although there is a vast array of BMPs described and known to one skilled in the art, BMPs 2, 4, 6 and 7 are generally considered to be the most osteoinductive.

The disclosed composition provides biodegradable synthetic bone graft materials to specifically preserve the solubility of osteoinductive proteins. Various forms of calcium phosphates are known to have different chemical affinities for endogenous osteoinductive proteins (e.g., BMPs). Calcium phosphates such as TCP and HA are known to strongly bind acid-soluble BMPs because of their alkaline surface chemistry. In contrast, dical presents a moderately acidic surface chemistry that will not bind acidic proteins. Because of its enhanced solubility, it can also moderately buffer the local environment to an acidic range that further preserves osteoinductive BMP solubility.

An in vitro study assessed the influence of variable composition calcium phosphate salts on the soluble concentration of osteoinductive proteins. The residual concentration of soluble recombinant BMP-2 was measured after exposing a controlled concentration aliquot to an equi-molar quantity of calcium phosphate salt. As shown in Table 2, moderately acidic calcium phosphates salts, such as dical, preserved the highest soluble concentration of osteoinductive proteins. The enhanced local concentration and cellular availability of bone morphogenetic proteins (BMPs) better stimulate bone formation.

TABLE 2

Equilibrium solubility of osteoinductive recombinant human BMP-2 protein in the presence of equimolar concentrations of various calcium phosphates.

|  | [rhBMP-2] mg/ml | [rhBMP-2] % |
| --- | --- | --- |
| Control | 15.0 | 100% |
| $Ca(H_2PO_4)_2$ (monocal) | 15.0 | 100% |
| $CaHPO_4$ (dical) | 11.4 | 76% |
| $Ca_3(PO_4)_2$ (TCP) | 3.5 | 23% |
| $Ca_5(PO_4)_3(OH)$ (HA) | 2.3 | 15% |

In one embodiment, an additive (e.g., an osteoinductive component) formulated as a putty or paste is included in the biocompatible composition that facilitates skeletal regeneration and provides a scaffold for new bone growth. Use of synthetic components reduces the potential of disease transfer and immune system incompatibilities. The terms putty and paste are qualitative and generally describe a composition that is moldable/formable and flowable, respectively. When the term paste is used to describe the composition including a liquid, it is to be understood that a putty may also be formed, generally by decreasing the volume of liquid mixed with the composition.

In one embodiment, the composition forms a paste that enhances the formation of bone tissue and increases the availability, and thus the functional activity of osteoinductive growth factors. It is provided at a surgical site during reconstruction of a skeletal defect. For example, the paste may be used in spine, dental, reconstructive, trauma, and other orthopedic surgeries. The paste may be used as a substitute for or additive to autologous bone grafts. Although the composition is synthetic, it may include natural components, e.g., bovine collagen, and/or be combined with natural components, e.g., bone marrow aspirate.

The paste controls pH to enhance clinical efficacy of osteoinductive proteins, and supplements local availability of bone components such as collagen, calcium, and phosphate. Without being bound by a specific theory and as analyzed above, moderately acidic microenvironments likely improve protein-stimulated osteoinduction by enhancing the degree of protein solubilization and protein release from collagen. Supplementing the local concentration of soluble $[Ca^{2+}]$ and $[PO_4^{3-}]$ ions increases the rate of bone formation by reducing dependence on ion diffusion from serum and other body fluids. The resultant increase in local concentration of collagen and mineral building blocks, coupled with the enhanced cellular availability of bone morphogenetic proteins, improves acidic collagen delivery vehicles.

In one embodiment, the composition formulated as a paste is both osteoinductive, i.e., it initiates or induces bone growth, and osteoconductive, i.e., it facilitates already initiated bone growth but does not itself initiate bone growth. Its osteoinductive effect arises, for example, from osteoinductive factors present in the liquid, e.g., bone marrow aspirate, used to make the paste. The composition is also osteoinductive in that it does not inhibit or diminish the solubility of osteoinductive factors, such as BMPs, due to the ability of the composition to induce a local pH decrease, as analyzed above. Its osteoconductive effect arises from provision of a collagen scaffold and source of bone growth materials. In one embodiment, exogenous osteoinductive factors are included as additives in the composition.

A variety of calcium phosphate salts, represented by the general chemical formula $xCaO, P_2O_5$ may be used to simultaneously supplement the local $[Ca^{2+}]$ and $[PO_4^{3-}]$ ion concentrations and to act as short-term biologic buffers. In one embodiment, the composition includes a particulate formed from crosslinked collagen and calcium phosphate.

In another embodiment, a method of making the particulate composition is provided. Collagen and calcium phosphate are combined, dried, crosslinked, and particulated as subsequently described.

In another embodiment, a method of using the collagen and calcium phosphate particles is disclosed. The particulate composition can be combined with a fluid, for example bone marrow aspirate, to create a paste. The paste is then injected, manually applied, or otherwise delivered to a site of a bone. In one embodiment, the paste is an injectible bone void filler. The paste provides improved handling and delivery capabilities, allowing a surgeon to introduce the composition into complex geometry bone defects. The paste components are fully resorbable and stimulate bone regeneration in a manner similar to that achieved with natural bone.

In one embodiment, the composition contains particulate, fibrillar collagen and calcium phosphate. The composition can be combined with a liquid such as biological fluids (e.g., bone marrow aspirate, whole blood, serum, plasma, etc.) to form a paste. The paste is then used as an injectible and/or conformable (i.e., moldable) bone-grafting material for primary applications in, e.g., spine fusion, dental furcation augmentation, fracture repair, etc.

In one embodiment, where a fibrillar collagen component is combined with a calcium phosphate component to produce a mineralized collagen component, porous particles of the mineralized collagen component may be prepared. In one embodiment, particle porosity measured as the total open pore volume is greater than about 90 percent by volume. In another embodiment, the total open pore volume within the particle ranges from about 50 percent to about 97 percent. In one embodiment, particle pore size ranges from about 1 µm to about 1000 µm. In another embodiment, particle pore sizes range from about 125 µm to about 300 µm. In one embodiment, the particle size ranges from about 100 µm to about 840 µm.

A variety of calcium phosphate salts, represented by the general chemical formula $Ca_x(PO_4)_y(O,OH,H_2O)$, may be used in the product composition to simultaneously supplement the local concentration of $[Ca^{2+}]$ and $[PO_4^{3-}]$ ion concentrations and to act as short-term biologic buffers. Calcium phosphates that may be used in the composition include monocalcium phosphate (monocal) $[Ca(H_2PO_4)_2]$, calcium hydrogen phosphate (dical) $[CaHPO_4]$, calcium pyrophosphate $[2CaO.P_2O_5]$, tricalcium phosphate $[3CaO.P_2O_5]$, hydroxyapatite $[3.33\ CaO.P_2O_5(OH)_2$ (polycrystalline and amorphous compositions)], tetracalcium phosphate $[4CaO.P_2O_5]$ and calcium carbonate $[CaCO_3$(aragonite), $CaCO_3$ (calcite)]. In one embodiment, the composition comprises an acidic mixture of calcium phosphates. Acidic calcium phosphate refers to those compositions, with composite calcium (x)/phosphate (y) below 1.5, that either present acidic surface chemistries or solubilize in aqueous solution to a sufficient extent to cause solution buffering to an acidic value (pH<7.0). In one embodiment, the acidic calcium phosphate is calcium hydrogen phosphate dihydrate [$CaHPO_4 \cdot 2H_2O$]. In one embodiment, the acidic calcium phosphate is anhydrous calcium hydrogen phosphate [$CaHPO_4$]. In one embodiment, the calcium phosphate of the composition is greater than about 25 percent by dry weight. In another embodiment, the calcium phosphate of the particulate composition is about 67 percent by dry weight.

The composition may further comprise additives such as bioactive agents, e.g., agents that exhibit biologic activity, and liquids. For example, agents that are osteoinductive and/or osteogenic may be included. As previously stated, osteoinductive agents stimulate bone growth. Examples of osteoinductive agents include bone growth factors, bone marrow components, blood components, and bone components.

Bone growth factors may be purified or recombinant and include bone morphogenetic protein (BMP). Bone marrow aspirates (BMA) may be used in the composition because they contain osteoinductive agents such as bone growth factors and mesenchymal stem cells. Mesenchymal stem cells (MSCs) are multi-potent cells capable of differentiating along several lineage pathways to aid in the production of bone. MSCs are considered as a readily available source of cells for many tissue engineering and regenerative medicine applications. For these reasons, osteoinductive proteins and MSCs have been used to supplement the performance of osteoconductive bone formation scaffolds as replacements for autologous and allogeneic bone grafts.

In one embodiment, bone marrow aspirate is included in the composition. Blood components such as whole blood and platelet-rich plasma, may be included in the composition. Osteoinductive bone components that may be included in the composition include demineralized bone and autologous bone. Demineralized bone refers to bone that has been treated to remove all or a majority of the calcium phosphate mineral components. Demineralization is usually performed by exposing powdered bone, from any human or mammalian source, to acidic solutions (i.e., HCl, acetic acid, ethylene diamine tetracetic acid) with a pH less than about 4. Bone that has not been demineralized may be included in the composition and also includes bone derived from an autologous or mammalian source.

Adding liquid to the composition results in a paste or putty, defined as soft masses with physical consistencies between a liquid and a solid. The liquid may be a biological fluid such as blood, plasma, serum, bone marrow, etc., or may be a buffer or may be capable of buffering to the physiological pH values of human serum (pH 7.1 to pH 7.4). Examples of buffers are known to one skilled in the art and include Tris and phosphate-buffered saline. In one embodiment, the composition has a pH in the range of about pH 5 to about pH 7.4. In another embodiment, the composition has a pH in the range of about pH 5.5 to about pH 6.9.. More than one liquid may be included in the composition. For example, the composition may include bone marrow aspirate and a buffering salt solution. The liquid may also include biocompatible liquids such as water, saline, glycerin, surfactants, carboxylic acids, dimethylsulfoxide, and/or tetrahydrofuran. In one embodiment, the liquid is greater than about 25 percent by volume of the composition. In another embodiment, the liquid comprises from about 75 percent to about 90 percent by volume of the composition. Additionally, natural and synthetic polymers such aliphatic polyesters, polyethylene glycols, polyanhydrides, dextran polymers, and/or polymeric orthophosphates may be included in the composition.

In one embodiment, a process for producing a particulate mineralized collagen composition comprising collagen and calcium phosphate is provided. In one embodiment, a crosslinked collagen and calcium phosphate composition is prepared and is then formed into particles, as shown in FIG. 2. Initially, collagen and calcium phosphate are combined with an acid, e.g. HCl, to create a slurry. The slurry may also be a gel due to the presence of collagen in an acidic environment. The types of collagen that may be used are described above and include bovine dermal fibrillar collagen. Suitable calcium phosphate includes acidic calcium phosphate such as monocalcium phosphate [$Ca(H_2PO_4)_2$], calcium hydrogen phosphate [$CaHPO_4$], and/or calcium pyrophosphate [$2CaO \cdot P_2O_5$]. In one embodiment, about 33 percent by weight of collagen is combined with about 67 percent by weight calcium phosphate.

The combination is then subjected to freezing, lyophilization, and crosslinking. In one embodiment, the composition is frozen at about −80° C. for about two hours. In one embodiment, the composition is lyophilized for at least about sixteen hours. In another embodiment, the composition is lyophilized for at least about 48 hours.

The composition may be crosslinked. Crosslinking may be effected by a variety of methods known to one skilled in the art, including but not limited to dehydrothermal (DHT) crosslinking. In DHT crosslinking, the composition is placed in a vacuum oven chamber, the chamber is evacuated to create a vacuum, and the composition is heated for a period of time. In one embodiment, the composition is heated to about 110° C. In one embodiment, the composition is heated in a vacuum oven for about 48 hours.

Following freezing, lyophilization, and crosslinking, the solid composition is formed into particles. Methods of forming particles are known to one skilled in the art and include, but are not limited to, grinding, milling, chopping, and/or molding. In one embodiment, particles are formed by milling the solid composition. Milling may occur using a Wiley mill (Thomas Scientific, Swedesboro N.J.). The mesh size on the mill directs the size of the resultant particles. In one embodiment, a −20 mesh is used that creates particles in the range of about 100 µm to about 840 µm. The particles may be sized by, for example, sieving. At any point in the process, additional components may be added to the composition, as described above. For example, an osteoinductive component can be added prior to forming the articles.

The composition may be provided as a kit. In one embodiment, the kit includes the composition described above, and may further include other components. These include a receptacle such as a plastic container in which to place the composition and in which to add liquid to form the composition into a paste or putty, a mixing implement such as a spatula, stir rod, etc., a disposable syringe barrel without a needle in which to place and deliver the mixed paste, instructions for formulating and/or using the composition, etc.

In another embodiment, a method of facilitating bone growth is provided. In one embodiment, the method includes adding at least one osteoinductive component such as a purified bone growth factor, a recombinant bone growth factor, a bone marrow component, a blood component, demineralized bone, autologous bone, etc., to the particulate composition previously described. In embodiments where the osteoinductive component is bone marrow aspirate, blood, or a blood component, it may be acutely obtained and added to the composition (e.g., blood and/or bone marrow may be obtained from the same surgical site for repairing the defect). Adding the osteoinductive component(s) and/or another liquid to the composition, with stirring, results in a paste or putty, which is provided to the desired anatomical site of the patient.

In one embodiment, the paste is loaded into the barrel of a disposable 5 cc syringe, without a needle attached, and is extruded through the barrel aperture to the desired anatomical site. In another embodiment, the putty is manipulated or formed into a configuration of desired size, shape, length, etc., either manually or by instrumentation, and gently pressed on and/or in the desired anatomical site. The site is desirably prepared to expose healthy bleeding bone, facilitating subsequent bone growth. The method may be performed using minimally invasive procedures known to one skilled in the art. The method may be used in at least partially filling bone voids and/or gaps of the skeletal system (i.e., extremities, pelvis, spine, oral cavity) that are not intrinsic to the stability of the bone structure. These voids and/or gaps may be a result of trauma, either natural or by surgical creation. The paste is gently provided on and/or in the void and/or gap. The paste is resorbed by the body during the healing process (over days, weeks, and months). The paste may be molded into the bone void or defect by manipulating either manually or using an instrument (e.g., spatula, syringe, probe, cannula, etc.).

The following examples further illustrate embodiments of the invention.

EXAMPLE 1

A composite collagen and calcium phosphate gel dispersion was prepared (5 vol. % collagen gel) by weighing 6 g collagen. A 10 mM HCl solution was volumetrically measured (246 ml) to prepare a 5 vol. % gel. Twelve g sterilized dicalcium phosphate [$CaHPO_4$] powder (66.7 wt. % calcium phosphate) was added and stirred to a uniform consistency. The combination was mixed, for example, by repeated shear material transport, until a uniform collagen gel dispersion of moderate viscosity (about 1,000 P to about 1,500 P) was obtained.

About 16.5 ml of the collagen and calcium phosphate gel dispersion was then cast into an autoclaved TEFLON® mold of 4.5 cm (L)×1.7 cm (W)×2.1 cm (H), with removable upper and lower autoclaved glass plates. The collagen gel dispersion was injected into the mold with the lower glass plate attached and the composition was evenly spread using a spatula. The upper autoclaved glass plate was then fixed in contact with the dispersion and the plates were secured using countersunk flat head screws. The mold was then maintained at −80° C. for at least one hour.

After freezing, the glass plates were removed from both sides of the mold backing and the mold containing the frozen product was placed in a sterile paper autoclave pouch and frozen within a glass lyophilization vessel for two hours.

The frozen composition was then lyophilized (i.e. freeze-dried) at room temperature in a Laboratory Freeze Dryer (Freezemobile 25EL, VirTis Inc., Gardiner N.Y.) for at least 24 hours. The lyophilization vessel containing the product was attached to the vacuum port of the Freezemobile in operation with a condenser temperature of −50° C. or below, and a manifold pressure of $10^{-3}$ mm Hg or less. The vacuum port to the vessel was opened exposing the frozen product to pressure sufficient to freeze dry the product within 24 hours at room temperature.

The composition was then crosslinked via a dehydrothermal (DHT) process. The composition was removed from the mold and placed onto an autoclaved aluminum pan. The samples were then placed into a vacuum oven. The gas vents were closed and the chamber was evacuated to $10^{-3}$ mm Hg. The vacuum chamber was heated to 110° C. After 48 hours of constant temperature heating, the samples were cooled to room temperature (about 20° C. to about 22° C.) under vacuum. After the composition bar cooled, the chamber was repressurized with 0.2 micron filtered air. The composition bar was removed using sterile forceps and stored in a sterile paper autoclave pouch.

The samples were then processed into particles. Samples were placed into the hopper of a clean Wiley Mini-Mill (Thomas Scientific, Swedesboro N.J.), and milled at about 1,700 rpm. The samples were swept around by rotor until cut to sufficient fineness to pass through the sieve top of a delivery tube that formed the bottom of the chamber. The final product was collected using a 20 mesh delivery unit located under the mill blades.

In one embodiment, the particles were also subjected to compression molding to form storage disks. The particles were weighed and introduced into a cylindrical mold to produce solid disks through uni-axial compression. The compression pressure was optimized to simultaneously produce a solid product. This product resisted breakage during normal shipping and facilitated rapid product mixing (less than two min).

EXAMPLE 2

Prior to opening a container containing particles of the above composition, the volume of a bone void to be repaired was determined. Based on the bone void, an appropriate volume of non-human animal blood was obtained, using a ratio of 0.75:1 blood or bone marrow aspirate : bone void volume. Appropriate volumes of liquid were added, as subsequently described, to obtain products of desired cohesive consistency (e.g. paste). As one example, per 1 cc dry particle volume, 0.75 ml whole blood was added to obtain a cohesive putty, or 0.85 ml whole blood was added to obtain a paste. As another example, per 1 cc dry particle volume, 0.75 ml bone marrow aspirate was added to obtain a cohesive putty, or 0.85 ml bone marrow aspirate was added to obtain a paste.

Immediately prior to implantation on an isolated bone, the liquid was mixed with the composition to obtain a paste of desired consistency. The bone void site was irrigated as needed and the paste was packed into the bone void. The site was sealed with surrounding soft tissue as needed, e.g., to close the wound and restore soft tissue configuration. Rigid fixation of the defect site stabilized the bone void.

It should be understood that the embodiments and examples described are only illustrative and are not limiting in any way. Therefore, various changes, modifications or alterations to these embodiments may be made or resorted to without departing from the spirit of the invention and the scope of the following claims.

What is claimed is:

1. A biocompatible synthetic bone growth composition comprising a fibrillar collagen component, an acidic calcium phosphate component, and demineralized bone.

2. The composition of claim 1 wherein the fibrillar collagen component is obtained from a natural source.

3. The composition of claim 2 wherein the fibrillar collagen component is obtained from the group consisting of dermis, tendon, cartilage, or bone.

4. The composition of claim 2 wherein the fibrillar collagen component is obtained from a human source.

5. The composition of claim 1 wherein the fibrillar collagen component is synthetic.

6. The composition of claim 1 wherein the fibrillar collagen component is non-immunogenic.

7. The composition of claim 1 wherein the fibrillar collagen component is crosslinked.

8. The composition of claim 7 wherein the fibrillar collagen component is crosslinked by dehydrothermal crosslinking, UV light exposure, or chemical crosslinking.

9. The composition of claim 1 wherein the fibrillar collagen component has an in vivo lifetime of up to about twelve weeks.

10. The composition of claim 1 wherein the acidic calcium phosphate is selected from the group consisting of monocalcium phosphate $[Ca(H_2PO_4)_2]$, calcium hydrogen phosphate $[CaHPO_4]$, and calcium pyrophosphate $[2CaO.P_2O_5]$.

11. The composition of claim 10 wherein the acidic calcium phosphate is calcium hydrogen phosphate $[CaHPO_4]$.

12. The composition of claim 1 wherein the equilibrium solubility of calcium or phosphate ions is greater than that of a hydroxyapatite $[3.33CaO.P_2O_5(OH)_2]$.

13. The composition of claim 12 wherein the equilibrium solubility of calcium or phosphate ions is at least 200 times greater than that of hydroxyapatite $[3.33CaO.P_2O_5(OH)_2]$.

14. The composition of claim 1 wherein the demineralized bone comprises at least one osteoinductive protein.

15. The composition of claim 14 wherein the equilibrium solubility of the at least one osteoinductive protein in the presence of the acidic calcium phosphate component is greater than in the presence of an equi-molar quantity of a hydroxyapatite $[3.33CaO.P_2O_5(OH)_2]$ in the composition.

16. The composition of claim 15 wherein the equilibrium solubility of the osteoinductive protein is at least five times greater than in the presence of an equimolar quantity of hydroxyapatite $[3.33CaO.P_2O_5(OH)_2]$ in the composition.

17. The composition of claim 1 wherein the composition is moldable.

18. The composition of claim 1 wherein the composition is a paste.

19. The composition of claim 1 wherein the composition is a putty.

20. The composition of claim 1 wherein the composition is injectable.

21. The composition of claim 1 wherein the pH of the composition is between about 5 and about 7.

22. The composition of claim 1 comprising particles of fibrillar collagen and acidic calcium phosphate.

23. The composition of claim 22 wherein the particles comprise about 33% fibrillar collagen by weight and about 67% acidic calcium phosphate by weight.

24. The composition of claim 22 wherein the particles comprise between about 25% and about 75% fibrillar collagen by weight.

\* \* \* \* \*